United States Patent [19]
Schlegel et al.

[11] Patent Number: 5,874,089
[45] Date of Patent: Feb. 23, 1999

[54] PROTECTING AGAINST CANINE ORAL PAPILLOMAVIRUS (COPY)

[75] Inventors: C. Richard Schlegel; A. Bennett Jenson, both of Rockville, Md.; Shin-je Ghim, Washington, D.C.

[73] Assignee: Georgetown University School of Medicine, Washington, D.C.

[21] Appl. No.: 724,281

[22] Filed: Oct. 1, 1996

[51] Int. Cl.$^6$ .................................................. A61K 39/12
[52] U.S. Cl. ..................... 424/204.1; 424/192.1; 424/199.1; 424/184.1; 424/186.1; 435/5; 435/69.1; 435/69.3; 435/235.1; 435/240.2; 435/320.1; 536/23.72
[58] Field of Search ............................ 424/199.1, 192.1, 424/204.1, 184.1, 186.1; 435/5, 69.1, 69.3, 235.1, 240.2, 320.1; 536/23.72

[56] References Cited

U.S. PATENT DOCUMENTS 5,437,951  8/1995  Lony et al. ............................ 435/69.1

OTHER PUBLICATIONS

Bell et al. A formation–inactivated vaccine protects against Mucosal Papillomavirus infection: A canine model, Pathobiology 62: 194–198 (1994).

Delius et al. Canine oral papillomavirus genomic sequence: A unique 1.5Kb interveiwing sequence between the Ez and Lz open reading frames. Virology 204, 447–452 (1994).

*Primary Examiner*—Mary E. Mosher
*Assistant Examiner*—Ali R. Salimi
*Attorney, Agent, or Firm*—Burns, Doane, Swecker & Mathis, L.L.P.

[57] ABSTRACT

Recombinantly produced L1 major capsid proteins which mimic conformational naturalizing epitopes on human and animal papilloma virions including canine and equine papilloma virions are provided. These recombinant proteins are useful as vaccines for conferring protection against papillomavirus infection. Antibodies to the recombinant protein are also provided. Such antibodies are useful in the diagnosis and treatment of viral infection.

11 Claims, 8 Drawing Sheets

FIG. 5

PROTECTION OF DOGS AGAINST COPV INFECTION BY THE PASSIVE TRANSFER OF IMMUNOGLOBULIN

| Treatment Procedure | Number of dogs with tumors | Number of dogs |
|---|---|---|
| Infused with lactate Ringers solution | 4 | 4 |
| Infused with non-immune dog serum, 200 mg/kg | 4 | 4 |
| Infused with immune dog serum, 200 mg/kg | 0 | 4 |

FIG. 6

DOG VACCINATION STUDIES UTILIZING CONFORMATIONALLY-CORRECT L1 PROTEIN PURIFIED FROM RECOMBINANT-BACULOVIRUS INFECTED Sf9 CELLS

| Vaccination Procedure | #dogs with oral tumors |
|---|---|
| Buffer | 6/8 |
| Formaline-fixed wart extract | 0/8 |
| L1 | 0/8 |
| L1 + alum adjuvant | 0/8 |
| L1 + QS21 adjuvant | 0/8 |

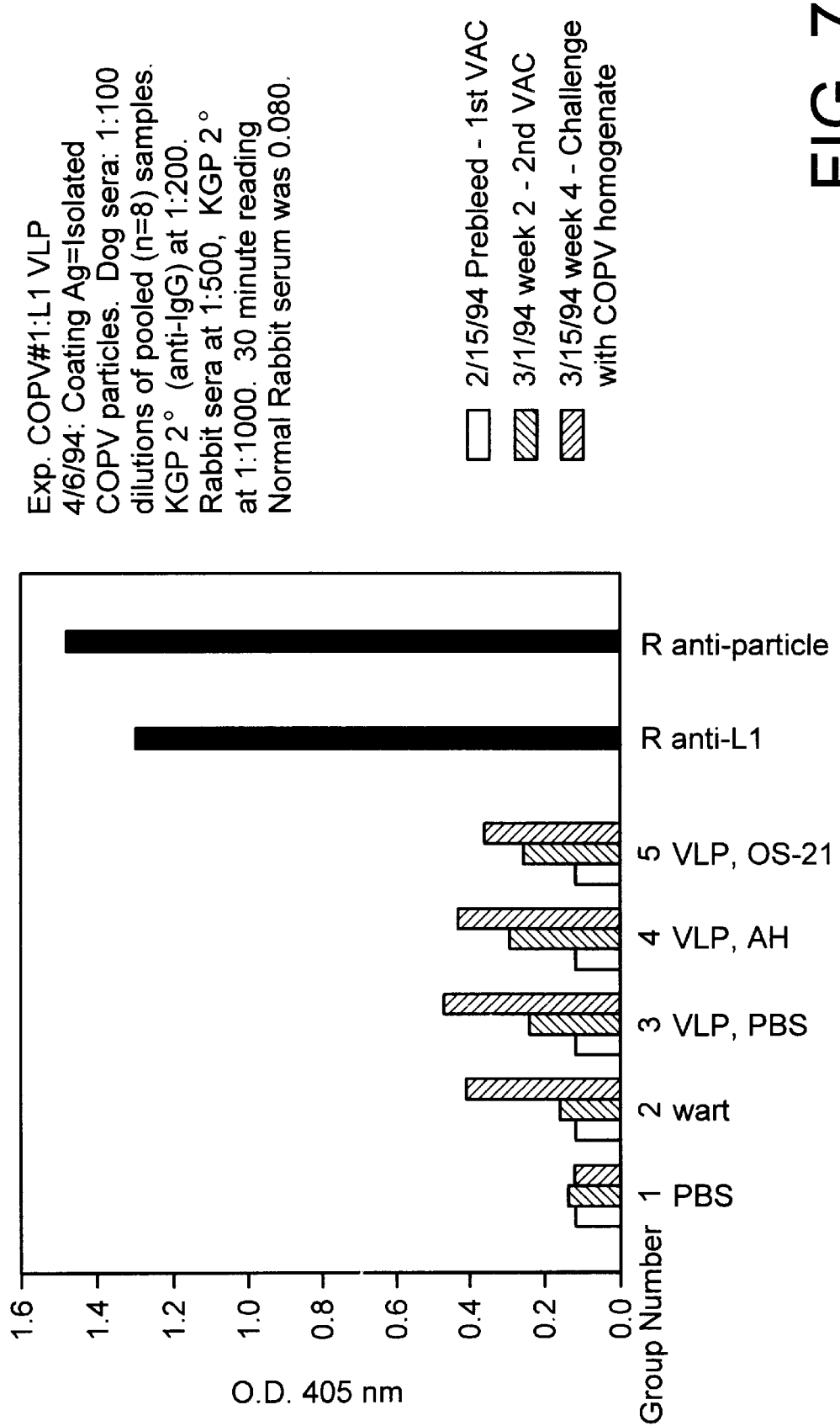

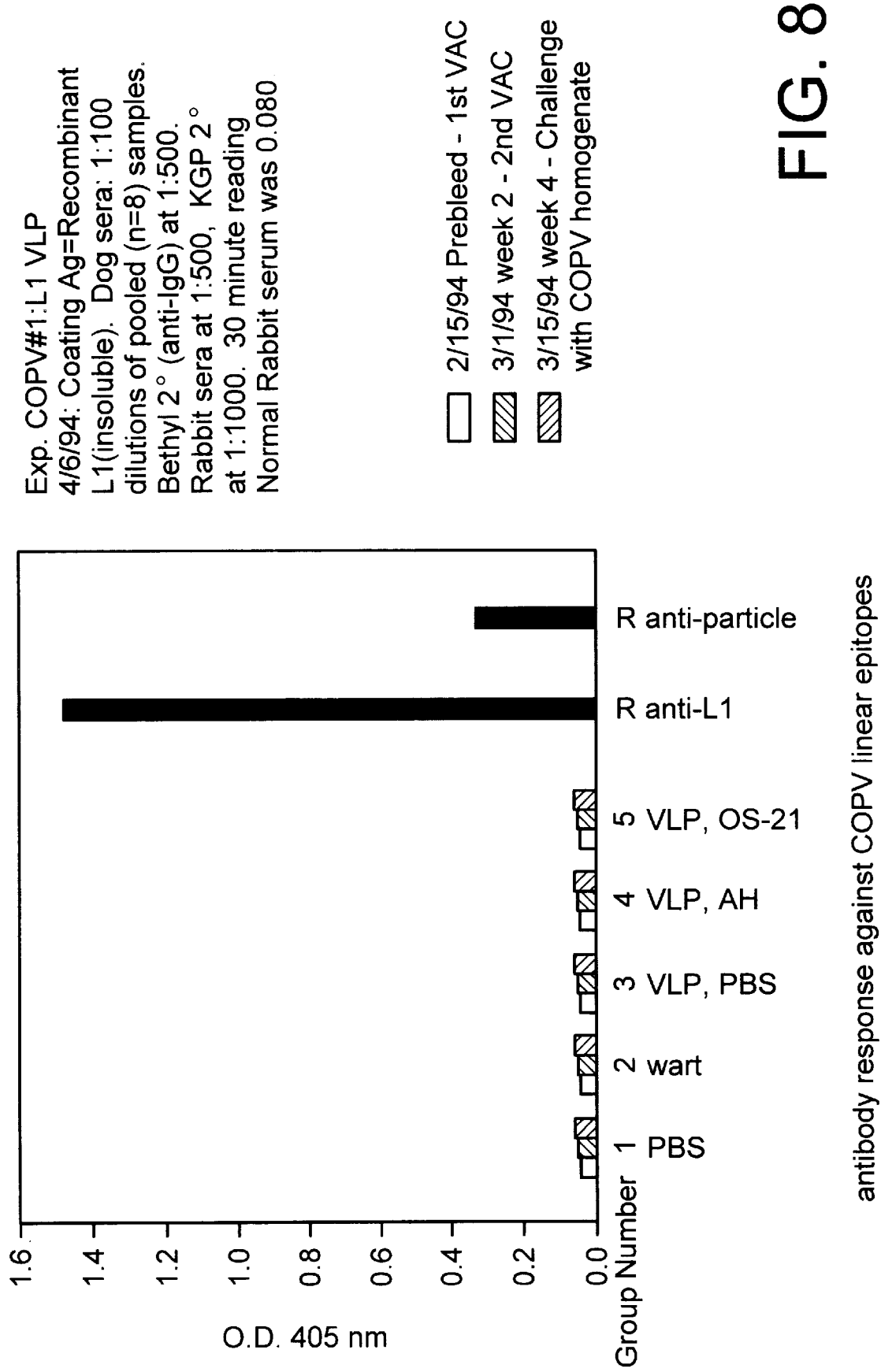

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 508 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:1:

```
Met Tyr Asn Val Phe Gln Met Ala Val Trp Leu Pro Ala Gln Asn Lys
  1               5                  10                  15
Phe Tyr Leu Pro Pro Gln Pro Ile Thr Arg Ile Leu Ser Thr Asp Glu
             20                  25                  30
Tyr Val Thr Arg Thr Asn Leu Phe Tyr His Ala Thr Ser Glu Arg Leu
         35                  40                  45
Leu Leu Val Gly His Pro Leu Phe Glu Ile Ser Ser Asn Gln Thr Val
     50                  55                  60
Thr Ile Pro Lys Val Ser Pro Asn Ala Phe Arg Val Phe Arg Val Arg
 65                  70                  75                  80
Phe Ala Asp Pro Asn Arg Phe Ala Phe Gly Asp Lys Ala Ile Phe Asn
                 85                  90                  95
Pro Glu Thr Glu Arg Leu Val Trp Gly Leu Arg Gly Ile Glu Ile Gly
                100                 105                 110
Arg Gly Gln Pro Leu Gly Ile Gly Ile Thr Gly His Pro Leu Leu Asn
            115                 120                 125
Lys Leu Asp Asp Ala Glu Asn Pro Thr Asn Tyr Ile Asn Thr His Ala
    130                 135                 140
Asn Gly Asp Ser Arg Gln Asn Thr Ala Phe Asp Ala Lys Gln Thr Gln
145                 150                 155                 160
Met Phe Leu Val Gly Cys Thr Pro Ala Ser Gly Glu His Trp Thr Ser
                165                 170                 175
Arg Arg Cys Pro Gly Glu Gln Val Lys Leu Gly Asp Cys Pro Arg Val
            180                 185                 190
Gln Met Ile Glu Ser Val Ile Glu Asp Gly Asp Met Met Asp Ile Gly
        195                 200                 205
Phe Gly Ala Met Asp Phe Ala Ala Leu Gln Gln Asp Lys Ser Asp Val
    210                 215                 220
Pro Leu Asp Val Val Gln Ala Thr Cys Lys Tyr Pro Asp Tyr Ile Arg
225                 230                 235                 240
Met Asn His Glu Ala Tyr Gly Asn Ser Met Phe Phe Phe Ala Arg Arg
                245                 250                 255
Glu Gln Met Tyr Thr Arg His Phe Phe Thr Arg Gly Gly Ser Val Gly
            260                 265                 270
Asp Lys Glu Ala Val Pro Gln Ser Leu Tyr Leu Thr Ala Asp Ala Glu
```

|  | 275 |  |  |  | 280 |  |  |  | 285 |  |  |  |
|---|---|---|---|---|---|---|---|---|---|---|---|---|

Pro Arg Thr Thr Leu Ala Thr Asn Tyr Val Gly Thr Pro Ser Gly
290                     295                     300

Ser Met Val Ser Ser Asp Val Gln Leu Phe Asn Arg Ser Tyr Trp Leu
305             310                 315                 320

Gln Arg Gly Gln Gly Gln Asn Asn Gly Ile Gly Trp Arg Asn Gln Leu
                325                 330                 335

Phe Ile Thr Val Gly Asp Asn Thr Arg Gly Thr Ser Leu Ser Ile Ser
            340                 345             350

Met Lys Asn Asn Ala Ser Thr Thr Tyr Ser Asn Ala Asn Phe Asn Asp
        355                 360             365

Phe Leu Arg His Thr Glu Glu Phe Asp Leu Ser Phe Ile Val Gln Leu
        370             375                 380

Cys Lys Val Lys Leu Thr Pro Glu Asn Leu Ala Tyr Ile His Thr Met
385                 390                 395                 400

Asp Pro Asn Ile Leu Glu Asp Trp Gln Leu Ser Val Ser Gln Pro Pro
                405                 410                 415

Thr Asn Pro Leu Glu Asp Gln Tyr Arg Phe Leu Gly Ser Ser Leu Ala
            420                 425             430

Ala Lys Cys Pro Glu Gln Ala Pro Pro Glu Pro Gln Thr Asp Pro Tyr
        435                 440                 445

Ser Gln Tyr Lys Phe Trp Glu Val Asp Leu Thr Glu Arg Met Ser Glu
    450                 455                 460

Gln Leu Asp Gln Phe Pro Leu Gly Arg Lys Phe Leu Tyr Gln Ser Gly
465                 470                 475                 480

Met Thr Gln Arg Thr Ala Thr Ser Ser Thr Thr Lys Arg Lys Thr Val
                485                 490                 495

Arg Val Ser Thr Ser Ala Lys Arg Arg Arg Lys Ala
        500                 505

(2) INFORMATION FOR SEQ ID NO:2:

(i) SEQUENCE CHARACTERISTICS:
        (A) LENGTH: 503 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

Met Ala Val Trp Leu Pro Ala Gln Asn Lys Phe Tyr Leu Pro Pro Gln
1               5                   10                  15

Pro Ser Thr Lys Val Leu Ser Thr Asp Glu Tyr Val Ser Arg Thr Asn
            20                  25                  30

Ile Phe Tyr His Ala Ser Ser Glu Arg Leu Leu Thr Val Gly His Pro
        35                  40                  45

Phe Tyr Glu Ile Tyr Lys Glu Glu Arg Ser Glu Val Ile Val Pro
    50                  55                  60

Lys Val Ser Pro Asn Gln Tyr Arg Val Phe Arg Leu Leu Leu Pro Asp
65                  70                  75                  80

Pro Asn Asn Phe Ala Phe Gly Asp Lys Ser Leu Phe Asp Pro Glu Lys
                85                  90                  95

Glu Arg Leu Val Trp Gly Leu Arg Gly Leu Glu Ile Gly Arg Gly Gln
            100                 105                 110

Pro Leu Gly Ile Ser Val Thr Gly His Pro Thr Phe Asp Arg Tyr Asn
        115                 120                 125

```
Asp  Val  Glu  Asn  Pro  Asn  Lys  Asn  Leu  Ala  Gly  His  Gly  Gly  Gly  Thr
     130                 135                      140

Asp  Ser  Arg  Val  Asn  Met  Gly  Leu  Asp  Pro  Lys  Gln  Thr  Gln  Met  Phe
145                      150                 155                           160

Met  Ile  Gly  Cys  Lys  Pro  Ala  Leu  Gly  Glu  His  Trp  Ser  Leu  Thr  Arg
               165                      170                           175

Trp  Cys  Thr  Gly  Gln  Val  His  Thr  Ala  Gly  Gln  Cys  Pro  Pro  Ile  Glu
               180                 185                           190

Leu  Arg  Asn  Thr  Thr  Ile  Glu  Asp  Gly  Asp  Met  Val  Asp  Ile  Gly  Phe
          195                      200                 205

Gly  Ala  Met  Asp  Phe  Lys  Ala  Leu  Gln  His  Tyr  Lys  Ser  Gly  Val  Pro
     210                      215                 220

Ile  Asp  Ile  Val  Asn  Ser  Ala  Cys  Lys  Tyr  Pro  Asp  Tyr  Leu  Lys  Met
225                      230                 235                           240

Ala  Asn  Glu  Pro  Tyr  Gly  Asp  Arg  Cys  Phe  Phe  Phe  Val  Arg  Arg  Glu
               245                      250                           255

Gln  Leu  Tyr  Ala  Arg  His  Ile  Met  Ser  Arg  Ser  Gly  Thr  Gln  Gly  Leu
               260                 265                      270

Glu  Pro  Val  Pro  Lys  Asp  Thr  Tyr  Ala  Thr  Arg  Glu  Asp  Asn  Asn  Ile
          275                 280                      285

Gly  Thr  Thr  Asn  Tyr  Phe  Ser  Thr  Pro  Ser  Gly  Ser  Leu  Val  Ser  Ser
     290                 295                      300

Glu  Gly  Gln  Leu  Phe  Asn  Arg  Pro  Tyr  Trp  Ile  Gln  Arg  Ser  Gln  Gly
305                      310                 315                           320

Lys  Asn  Asn  Gly  Ile  Ala  Trp  Gly  Asn  Gln  Leu  Phe  Leu  Thr  Val  Val
               325                      330                           335

Asp  Asn  Thr  Arg  Gly  Thr  Pro  Leu  Thr  Ile  Asn  Ile  Gly  Gln  Gln  Asp
               340                      345                           350

Lys  Pro  Glu  Glu  Gly  Asn  Tyr  Val  Pro  Ser  Ser  Tyr  Arg  Thr  Tyr  Leu
          355                      360                      365

Arg  His  Val  Glu  Glu  Tyr  Glu  Val  Ser  Ile  Ile  Val  Gln  Leu  Cys  Lys
     370                      375                      380

Val  Lys  Leu  Ser  Pro  Glu  Asn  Leu  Ala  Ile  Ile  His  Thr  Met  Asp  Pro
385                      390                 395                           400

Asn  Ile  Ile  Glu  Asp  Trp  His  Leu  Asn  Val  Thr  Pro  Pro  Ser  Gly  Thr
               405                      410                           415

Leu  Asp  Asp  Thr  Tyr  Arg  Tyr  Ile  Asn  Ser  Leu  Ala  Thr  Lys  Cys  Pro
               420                      425                      430

Thr  Asn  Ile  Pro  Pro  Lys  Thr  Asn  Val  Asp  Pro  Phe  Arg  Asp  Phe  Lys
          435                      440                      445

Phe  Trp  Glu  Val  Asp  Leu  Lys  Asp  Lys  Met  Thr  Glu  Gln  Leu  Asp  Gln
     450                      455                 460

Thr  Pro  Leu  Gly  Arg  Lys  Phe  Leu  Phe  Gln  Thr  Asn  Val  Leu  Arg  Arg
465                      470                 475                           480

Arg  Ser  Val  Lys  Val  Arg  Ser  Thr  Ser  His  Val  Ser  Val  Lys  Arg  Lys
               485                      490                           495

Ala  Val  Lys  Arg  Lys  Arg  Lys
               500
```

PROTECTING AGAINST CANINE ORAL PAPILLOMAVIRUS (COPY)

This application claims benefit of priority to provisional application 60/004,691, filed Oct. 2, 1995.

FIELD OF THE INVENTION

The invention relates to the diagnosis, serotyping, prevention and treatment of viral diseases, particularly papillomavirus infections.

More particularly, the invention relates to the diagnosis, serotyping, prevention and treatment of human papillomavirus infections, equine papillomavirus infections and canine papillomavirus infections.

BACKGROUND OF THE INVENTION

Papillomaviruses (PV) are members of the papovavirus family and contain a double stranded circular DNA genome with a typical size of about 7900 base pairs (bp). Human papillomaviruses (HPV) are recognized as a cause of various epithelial lesions such as warts, condylomas and dysplasias. See, Gissman, L., Cancer Survey, 3:161 (1984); Boshart et al, ENBO J., 3:1151 (1984); Romanczuk et al, J. Virol., 65:2739–2744 (1991); Jenson et al, In "Papillomaviruses and human cancer" (H. Pfister. Ed.), pp. 11–43, CRC Press (1990); Schlegel, R., "Papillomaviruses and human cancer" In: Viral pathogenesis (ed. Fujinami, R.), Seminars in Virology 1:297–306 (1990); and Jenson et al, "Human Papillomaviruses" In Belshe, R. ed. Textbook of human virology, Second Edition: MASS:PSG, 1989:951.

HPVs are grouped into types based on the similarity of their DNA sequence. Two HPVs are taxonomically classified as being of the same type if their DNAs cross-hybridize to greater than 50% as measured by hybridization in solution under moderately stringent hybridization conditions.

A number of distinct papillomaviruses have been shown to infect humans. Papillomaviruses are highly species and tissue-specific, and are characterized by a specific mode of interaction with the squamous epithelia they infect. These small DNA tumor viruses colonize various stratified epithelia like skin and oral and genital mucosa, and induce the formation of self-limiting benign tumors known as papillomas (warts) or condylomas. These tumors are believed to arise from an initial event in the infectious cycle where the virus enhances the division rate of the infected stem cell in the epithelial basal layer, before it is replicated in the differentiating keratinocyte.

The term papillomavirus covers a large number of viruses which are considered responsible for several forms of viral infection ranging from relatively benign warts of the skin or mucous membranes to hyperplasias susceptible to progressing into dysplasias or intra-epithelial neoplasms, and malignant conversion to various forms of cancer, the most significant being that of the female uterine cervix.

A number of HPVs types have been identified. Furthermore, the preferential association of certain HPV types with anatomic location and distinct types of lesions gives support to the hypothesis that different HPV-induced lesions constitute distinct diseases, and that the clinical patterns of lesions express specific biological properties of distinct types of HPVs. Distinctive histological features have been associated with the infection of the skin or mucous membranes by different types of HPVs.

The genomes of different HPV types have been cloned and characterized. In particular, the genomes of two HPV types, HPV 16 and HPV 18, have been found to be associated with about 70% of invasive carcinomas of the uterine cervix.

Human papillomaviruses which infect the genital tract mucosa play a critical role in the development of cervical cancer. See, Lorincz et al, Obstetrics & Gynecology, 79:328–337 (1992); Beaudenon et al, Nature, 321:246–249 (1986); and Holloway et al, Gynecol. Onc., 41:123–128 (1991). For example, the majority of humans cervical carcinomas (95%) contain and express HPV DNA and it is the expression of two viral oncoproteins, E6 and E7, which appears to be critical for cellular transformation and maintenance of the transformed state. Despite the detailed knowledge concerning the molecular mechanism of action of these oncoproteins, there is little information available on the biology of papillomavirus infection, including the identity of viral receptors, the control of viral replication and assembly, and the host immune response to virus and virally-transformed cells. An effective vaccine against HPV infection could potentially reduce the incidence of human cervical dysplasia and carcinoma by 90–95%. However, there is no tissue culture system which permits sufficient keratinocyte differentiation to propagate the PV in-vitro. Because of the widespread occurrence of HPV infection, methods for detecting, preventing and treating viral infection are needed. Also, methods for detecting, preventing and treating papillomavirus infection in animals, e.g., equines and canines, are also needed.

Canine papillomas were one of the first animal systems studied when McFaydean and Hobday transmitted the oral papilloma in 1898. Today, dogs are commonly used as models for a variety of diseases and much is known about their physiology and immune system. Papillomas affect many anatomic locations in dogs, similar to the human diseases. Puppies may have marginal papillae on their tongues which are normal anatomic structures resembling oral papillomas. True papillomas can be found on the dorsal tongue and buccal mucosa, ocular mucous membranes, mucous membranes of the lower genital tracts of both males and females, and haired skin. The lesions are characterized by epithelial proliferation on thin fibrovascular stalks and there may be specific cytopathic effects in the stratum granulosum in which the cells swell, develop large keratohyalin-like granules, and may have intranuclear inclusions. Group-specific papillomavirus antigens can be detected by the cells exhibiting cytopathic effects.

The canine oral papillomavirus has been cloned and characterized (Sundberg et al, Amer. J. Vet. Res., 47(5), 1142–1177 (1986)). The COPV viral genome was cloned into pBR322, a restriction map constructed, with the completeness of the COPV genome confirmed by comparison of restriction fragment sizes derived from cloned and virion DNA. (Id.) It is known that COPV is antigenically similar to other papillomaviruses. For example, it has been reported that some of the antigenic and immunogenic epitopes of HPV16 and bovine, canine and avian papillomaviruses are shared. (Dillner et al, J. Virol., 65(12), 5862–6871, (1991)).

Strong evidence suggests that canine papillomaviruses play a role in squamous cell carcinoma development. For example, papillomavirus antigens are detected in penile and vulvar carcinomas. Also, it has been reported that intramuscular injection of canine oral papillomavirus results in the later development of cutaneous squamous cell carcinoma.

Papillomas are also prevalent in equines. In fact, papillomas are probably the most common equine tumor; however, few are ever submitted to diagnostic laboratories for histologic confirmation. Papillomas in equines generally affect the skin, mouth, lower genital tract and eyes. Papillomavirus which causes infection in equines is of the cutaneous type. Equine papillomaviruses have also been isolated and cloned. It is also known that equine papillomavirus infection causes millions of dollars in losses annually to the equine industry. Thus, based on the foregoing, it is clear that there exists a need for effective vaccines against papillomaviruses including HPV's and animal papillomaviruses such as COPV and equine papillomavirus.

SUMMARY OF THE INVENTION

Toward that end, a recombinantly produced L1 major capsid protein which mimics conformational neutralizing epitopes on human and animal papilloma virions is provided. The recombinant protein reproduces the antigenicity of the intact, infectious viral particle. The recombinant protein can be utilized to immunoprecipitate antibodies from the serum of patents infected or vaccinated with PV. Neutralizing antibodies to the recombinant protein are also provided. The antibodies are useful for the diagnosis and treatment of papilloma viral infection. The invention additionally provides subviral vaccines for the prevention of human and animal papillomavirus infection, e.g., for preventing equine and canine papillomavirus infection.

More specifically, recombinantly provided L1 major capsid proteins which mimic the conformational neutralizing epitopes on human, equine and canine papilloma virions are provided. These recombinant capsid proteins reproduce the antigenicity of the intact infectious human, canine or equine virus particle. The recombinant proteins can be utilized to immunoprecipitate antibodies from the serum of humans, equines or canines infected or vaccinated with the corresponding PV. Neutralizing antibodies to the human, canine or equine papillomavirus capsid protein are also provided. These antibodies are useful for the diagnosis and treatment of is human, canine or equine papilloma viral infections. The invention further provides subviral vaccines for the prevention of human, canine and equine papillomavirus infection.

The invention further provides a unique and relevant canine animal model for the development of papillomavirus vaccines, in particular canine and human papillomavirus vaccines; which unlike the available rabbit and bovine papillomavirus models, utilizes the canine oral papillomavirus (COPV) which is tropic for mucous membranes and is assayable for infectivity under normal conditions of exposure.

Purified HPV-1 virions were denatured with SDS and their constituent proteins separated by SDS polyacrylamide gel electrophoresis. The HPV-1 proteins were then transferred electrophoretically to nitrocellulose and reacted with 1:100 dilutions of the rabbit antisera or monoclonal antibodies (ascites fluid). MAB45, which was produced as a hybridoma supernatant, was only diluted 1:10. Primary antibody reactivity was detected using alkaline phosphatase-labelled goat anti-rabbit or anti-mouse IgG (Bio-Rad) at a dilution of 1:1000 in PBSA. Only rabbit antiserum #3 and MAB45, which both recognize denatured HPV-1 virions by ELISA, were found to react significantly with denatured L1 protein (see arrow).

Figure 2:
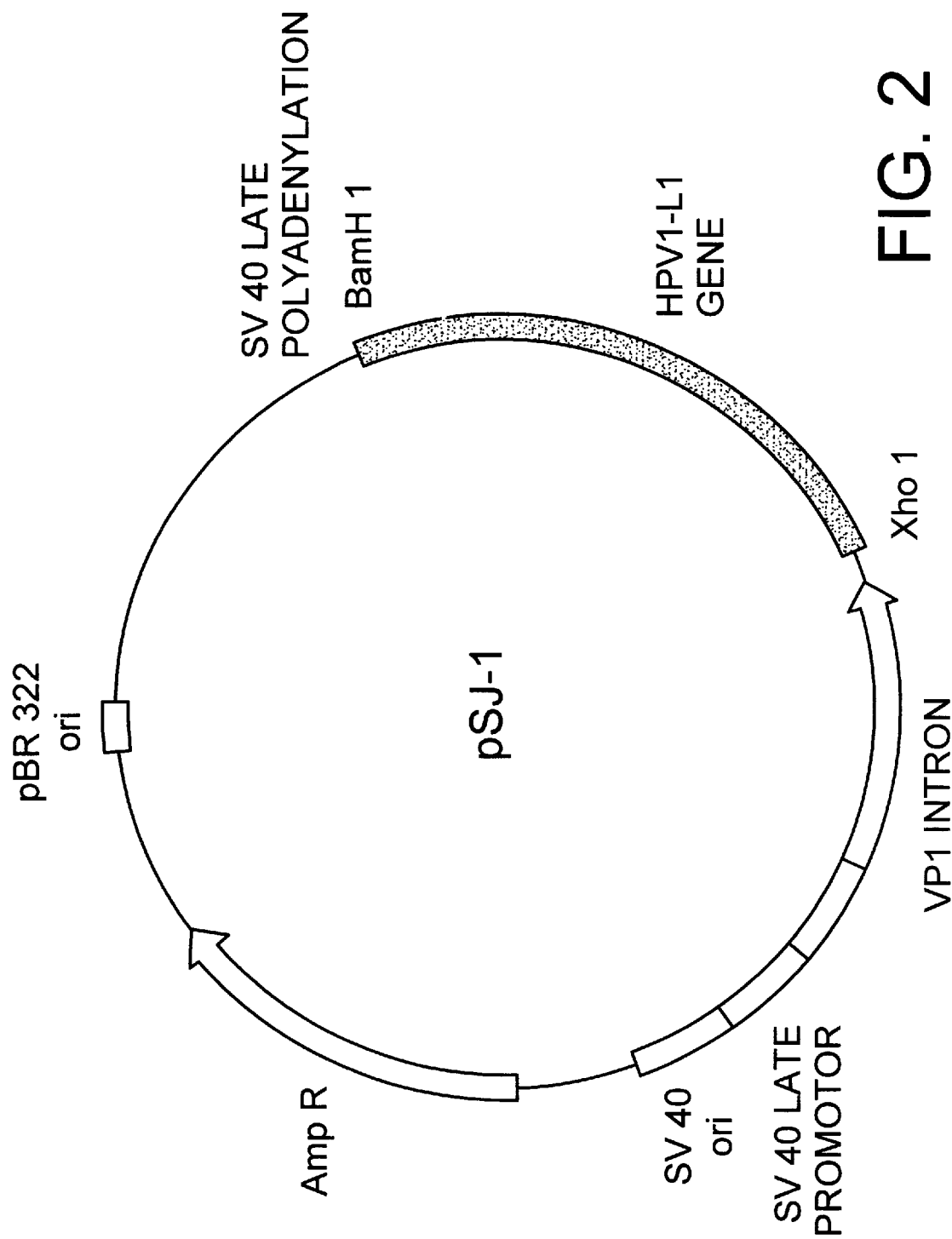

FIG. 2. Construction of SV40 vector, pSJ-1, which expresses the HPV-1 L1 gene.

The L1 gene of HPV-1 was amplified from cloned HPV-1 DNA using 5' and 3' oligonucleotide primers which contained XhoI and BamHI enzyme restriction sites, respectively. The plasmid, designated pSJ-1, contained the HPV-1 L1 gene expressed by the SV40 late promoter. The plasmid also contained the SV40 origin of replication (ori) as well as the SV40 VP1 intron and late polyadenylation signals. The entire pSJ-1 L1 gene was sequenced in its entirety and found to be identical to the genomic HPV-1 L1 sequence.

Figure 3:
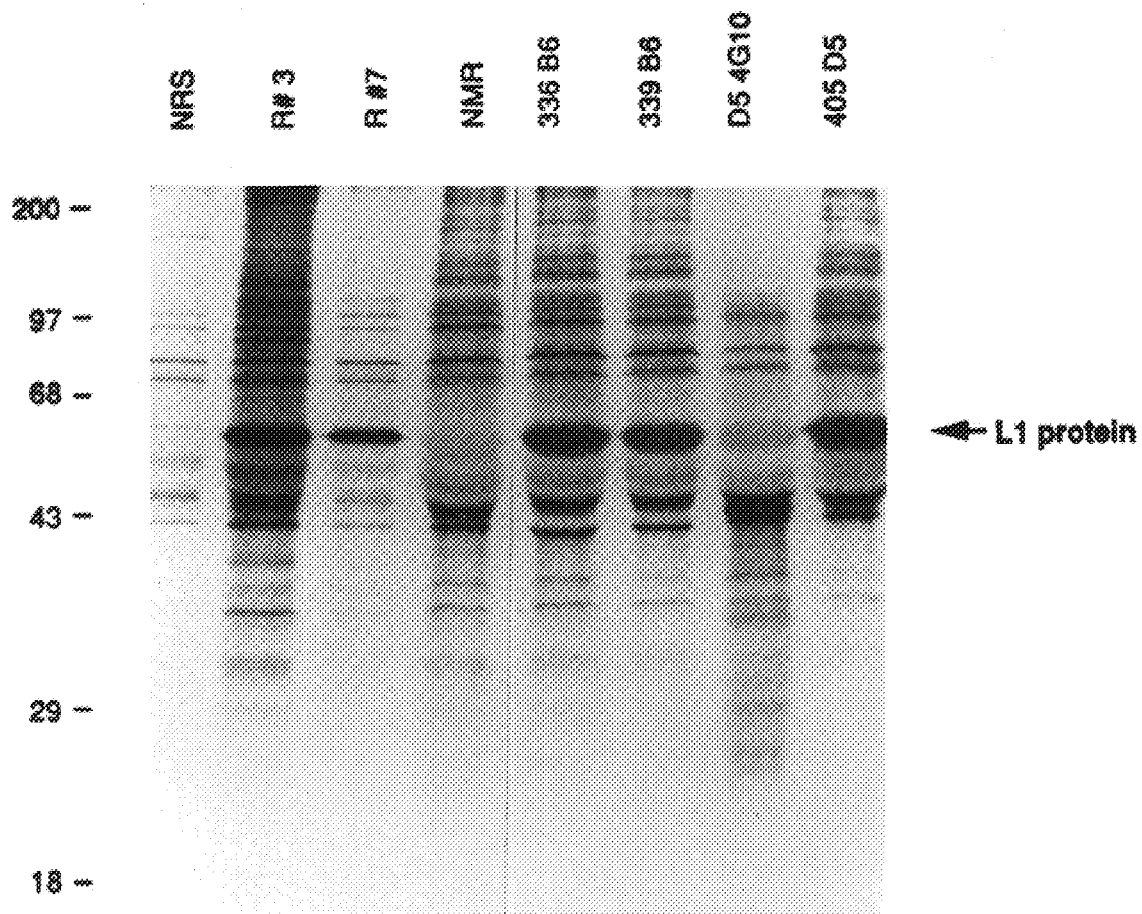
Figure 4A:
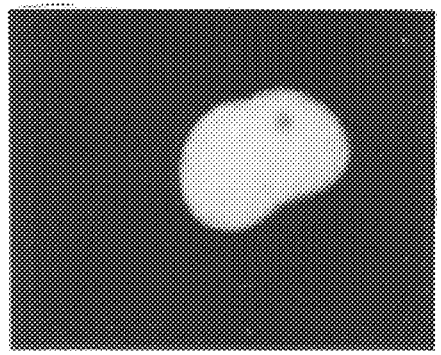
Figure 4B:
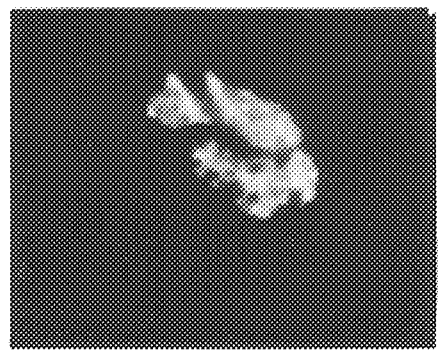
Figure 4C:
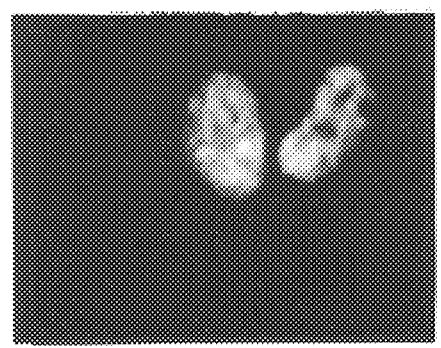
Figure 4D:
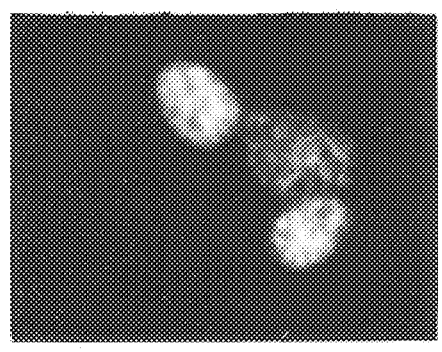
Figure 4E:
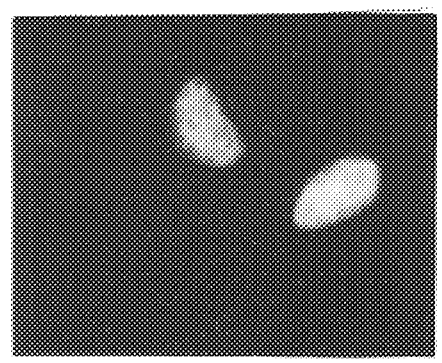
Figure 4F:
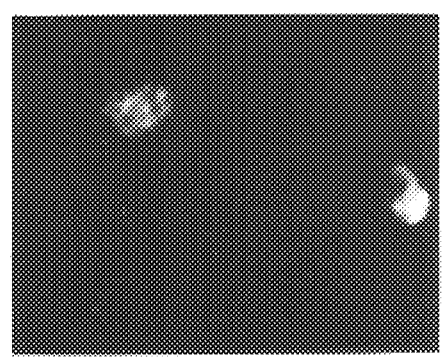
Figure 4G:
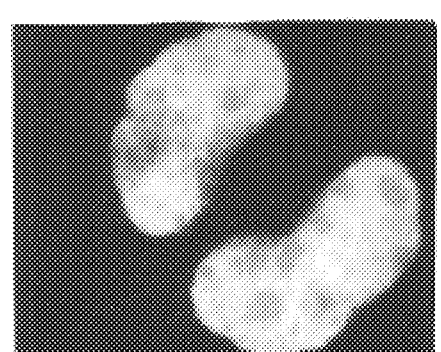
Figure 4H:
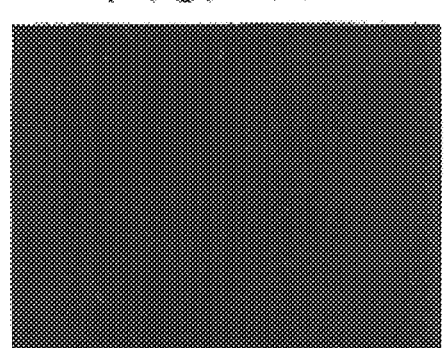

FIG. 3. Immunoprecipitation of HPV-1 L1 protein from COS cells transfected with pSJ-1.

COS cells, grown in 10 cm diameter plastic plates, were transfected when 80% confluent with 10 $\mu$g pSJ-1 plasmid DNA using a calcium phosphate precipitation technique (Graham, F. L., and van der Eb., A. J., Virology 52:456–467 (1973). 48 hr later, the cells were metabolically labelled with 500 $\mu$Ci/ml$^{35}$S-methionine for 4 hr in 2.5 ml cysteine and methionine-free medium. The cells were then washed with PBS, extracted with RIPA buffer, and immunoprecipitated with the indicated rabbit antisera or mouse monoclonal antibodies. The immunoprecipitated proteins were then analyzed by SDS-gel electrophoresis and autoradiography. All immune polyclonal antisera and monoclonal antibodies were able to immunoprecipitate L1 protein (see arrow). Lanes 1 and 4 show the absence of L1 protein when extracts were precipitated with either non-immune rabbit serum (lane 1) or with non-immune murine serum (lane 4).

FIGS. 4A–4H. Immunofluorescent staining of cos cells transfected with pSJ-1.

COS cells grown on glass coverslips were transfected with 10 $\mu$g pSJ-1 as described in FIG. 3. After 48 hr, the coverslips were washed with PBS, fixed in cold acetone, and reacted with 1:250 dilutions of rabbit antisera or mouse monoclonal antibodies. The reacted primary antibodies were stained with FITC-labeled goat anti-IgG at the dilution of 1:10 in PBS (Cappel). Nuclei of approximately 5–10% of transfected cos cells were positive by immunofluorescence. The evaluated antibodies were R#3 (panel a), R#7 (panel b), MAB45 (panel c), 334B6 (panel d), 339B6 (panel e), D54G10 (panel f), and 405D5 (panel g). All antisera were non-reactive with cos cells transfected with the parent pSVL vector lacking the HPV-1 L1 gene, including R#3 (panel h).

FIG. 5 contains results of an experiment wherein beagle dogs were administered serum obtained from beagle dogs vaccinated with a formalin-inactivated canine oral papillomavirus (COPV) L1 protein; or were administered serum from non-immune beagles, or lactate Ringers solution. The results show that the dogs administered the immune dog serum did not show any sign of papillomas after challenge with live infectious COPV, whereas both the group administered non-immune serum or lactate Ringers solution developed papillomas.

FIG. 6 contains results of an experiment wherein a first control group of dogs were mock vaccinated with PBS (Group I), a second group vaccinated with formalin-fixed wart homogenates (Group II), a third group vaccinated with 20 $\mu$g L1 contained in PBS (Group III), a fourth group with 20 $\mu$g of L1 protein contained in alum (Group IV), and a fifth group with 20 $\mu$g L1 protein in QS21 adjuvant (Group V) (wherein the COPV L1 protein was produced in recombinant baculovirus infected S9 cells).

FIGS. 7 and 8 contain the results of an experiment wherein the antibody response against both linear and conformational COPV L1 epitopes were compared after a first vaccination, after a second vaccination, and after challenge with infectious COPV. In this experiment, the animal groups were administered at 8 and 10 weeks as follows: Group I mock vaccinated with 0.2 ml PBS; Group II vaccinated with 0.2 ml formalin-fixed wart homogenate; Group III vaccinated with 0.2 ml of a composition comprising 20 μg of L1 protein in PBS; Group IV vaccinated with 20 μg of a composition comprising L1 protein in PBS containing alum, and Group V vaccinated with 0.2 ml of a composition comprising 20 μg L1 protein in QS21 adjuvant.

DESCRIPTION OF THE PREFERRED EMBODIMENTS

Methods and compositions are provided for the prevention, detection and treatment of papillomavirus (PV) infection. The methods are based upon the production of a recombinant L1 major capsid protein which is capable of reproducing the conformational neutralizing epitopes on human and animal papillomavirus virions. The invention is further drawn to antigenic fragments of such recombinant L1 proteins.

Although papillomaviruses infect a wide variety of vertebrate species, they exhibit a remarkable conservation of genomic organization and capsid protein composition. Papillomaviruses consist of small (about 55 nm), non-enveloped virions which surround a genome of double-stranded, circular DNA. The genome is approximately 8,000 bp in length and can be divided into equal-length "early" and "late" regions. The "early" region encodes 7–8 genes involved in such processes as viral DNA replication (the E1 and E2 genes), RNA transcription (the E2 gene), and cell transformation (the E5, E6 and E7 genes). The "late" region encodes two structural proteins, L1 and L2, which represent the major and minor capsid proteins, respectively. All of the "early" and "late" genes are transcribed from the same strand of viral DNA.

There are a variety of PV types known in the art. Further, particular types of PVs are associated with particular infections such as flat warts, cutaneous warts, epidermodysplasia verruciformis, lesions and cervical cancer. Over 50 different HPV types have been identified in clinical lesions by viral nucleotide sequence homology studies. See, for example, Jenson et al, "Human papillomaviruses" In: Belshe, R. ed., Textbook of human virology, Second Edition, MASS: PSG, 1989:951 and Kremsdorf et al, *J. Virol.,* 52:1013–1018 (1984). The HPV type determines, in part, the site of infection, the pathological features and clinical appearance as well as the clinical course of the respective lesion.

The L1 protein represents the most highly conserved protein of all the papillomavirus proteins. The nucleotide sequence of the L1 open reading frames of BPV-1, HPV-1A, and HPV-6B are given in U.S. Pat. No. 5,057,411, which disclosure is incorporated herein by reference. Furthermore, it is noted that L1 proteins and fusion proteins have been produced recombinantly. However, prior to the present invention, it was not known that L1 proteins with sufficient fidelity to maintain a conformation equivalent to that found in intact papillomavirus virions could be produced. Previously, recombinant L1 protein was produced as linear molecules which were incapable of protecting against papillomavirus infection. The present invention, in contrast, provides conformationally correct protein which is capable of inducing neutralizing antibodies which protect against animal and human papillomaviruses.

Because it is believed that there is little or no cross-immunity for PV types and immunity to infection is PV type-specific, it will be necessary to produce recombinant L1 protein for each specific PV type upon which protection or treatment is needed. However, due to the homology between the L1 proteins and genes, hybridization techniques can be utilized to isolate the particular L1 gene of interest. Nucleotide probes selected from regions of the L1 protein which have been demonstrated to show sequence homology, can be utilized to isolate other L1 genes. Methods for hybridization are known in the art. See, for example, *Nucleic Acid Hybridization, A Practical Approach,* IRL Press, Washington, D.C. (1985); *Molecular Cloning, A Laboratory Manual,* Maniatis et al, eds., Cold Spring Harbor Laboratory, Cold Spring Harbor, N.Y. (1982); and *Molecular Cloning, A Laboratory Manual,* Sambrook et al, eds., Cold Spring Harbor Laboratory, Second Edition, Cold Spring Harbor, N.Y. (1989). Alternatively, PCR methods can be utilized to amplify L1 genes or gene fragments. See, for example, U.S. Pat. Nos. 4,683,195; 4,683,202; and 4,800,159.

Virus particles can also be isolated for a particular papillomavirus type, the DNA cloned, and the nucleic acid sequences encoding L1 proteins isolated. Methods for isolation of viral particles and cloning of virus DNAs have been reported. See, for example, Heilman et al, *J. Virology,* 36:395–407 (1980); Beaudenon et al, *Nature,* 321:246–249 (1986); Georges et al, *J. Virology,* 51:530–538 (1984); Kremsdorf et al, *J. Virology,* 52:1013–1018 (1984); Clad et al, *Virology,* 118:254–259 (1982); DeVilliers et al, *J. Virology,* 40:932–935 (1981); and European Patent Application 0133123.

Alternatively, the L1 protein for a particular papillomavirus can be isolated, the amino acid sequence determined and nucleic acid probes constructed based on the predicted DNA sequence. Such probes can be utilized in isolating the L1 gene from a library of the papillomavirus DNA. See, for example, Suggs et al, *PNAS,* 78(11):6613–6617 (1981). See also, Young and Davis, *PNAS,* 80:1194 (1983).

Since the recombinant L1 protein must be of suitable conformation to mimic that of the intact virus particle, the expression system is crucial to the invention. An expression system must be utilized which produces L1 protein in the correct conformation. That is, the recombinant L1 protein reproduces the antigenicity of intact infectious virus particles. Such expression systems should also produce high levels of capsid protein. Generally, the expression system will comprise a vector having the L1 protein of interest and the appropriate regulatory regions as well as a suitable host cell. Typically a suitable host will be one which provides eucaryotic mechanisms for processing of the proteins.

Ideally, a strong promoter is utilized for high expression of the recombinant protein. Of particular interest is the pSVL vector. The pSVL vector contains an SV40 origin of replication and when transfected in COS cells, which express Large T antigen, replicates to a high copy number.

Alternatively, baculovirus vectors can be utilized. A baculovirus system offers the advantage that a large percentage of cells can be induced to express protein due to the use of infection rather than transfection techniques. While baculovirus is an insect virus and grows in insect cells (Sf9), these cells retain many of the eucaryotic mechanisms for processing of proteins including glycosylation and phosphorylation which may be important for generating proteins of appropriate conformation. Baculovirus vector systems are known in the art. See, for example, Summers and Smith, Texas Agricultural Experimental Bulletin No. 1555 (1987); Smith et al, *Mol. Cell Biol.,* 3:2156–2165 (1985); Posse, Virus Research, 5:4359 (1986); and Matsuura, J. Gen. Virol., 68:1233–1250 (1987).

In particular, this application exemplifies the expression of the canine oral papillomavirus (COPV) L1 protein in Sf9 cells using a baculovirus expression system and demonstrates that the resultant L1 proteins comprise conformational epitopes and confer protection when administered to naive dogs (beagles) upon challenge with live infectious COPV.

COPV was selected for several reasons. First, because of the high level of similarity between COPV and HPV's at the DNA and amino acid sequence level, genetic organizational level, as well as similar mucosal route of infection, COPV provides a highly suitable in vivo model for study of HPV vaccines. More specifically, dogs may be inoculated with COPV L1 proteins and challenged with live COPV in order to provide relevant in vivo evidence regarding the effectiveness of conformational PV L1 proteins to confer immunity against the corresponding papillomavirus.

While this is tremendously advantageous by itself, the COPV L1 protein is also important in its right. As discussed above, COPV is a mucosal papillomavirus which results in papillomas in canines that are found in dorsal tongue and buccal mucosa; ocular mucous membranes, mucous membranes of the lower genital tracts of both males and females, and haired skin. Moreover, COPV is believed to play a role in squamous cell carcinoma. Therefore, a vaccine against COPV is highly desirable because it may be used to prevent papillomas in canines, and also squamous carcinoma caused by COPV.

Moreover, given the substantial similarities between COPV and HPVs, in particular those which cause cancer in humans, the COPV/beagle animal model has applicability in screening the effectiveness of potential antiviral agents for treating human papillomavirus infection. Essentially, this will involve administering an antiviral agent predicted to be useful for treating human papillomaviral infection to a beagle dog which has been infected with COPV and ascertaining the effects of this antiviral agent on the status of COPV infection. This may be effected, e.g., by observing the size and number of papillomas in the treated animal before and after treatment with the antiviral agent. Antiviral agents which inhibit papilloma development or result in their decrease in size and/or number in treated animals should possess similar activity in humans for treating HPV infection given the similarities between COPV and HPVs.

Another animal PV where L1 conformational proteins have application in the design of vaccines is equine papillomavirus. As noted, equine papillomavirus is probably the most common cause of equine tumor. Squamous cell carcinomas, which are believed to be caused by equine papillomaviral infection, are also common in horses. This is substantiated by the fact that such carcinomas have an anatomic distribution similar to papillomas. One of the most common locations of such carcinomas is the lower genital tract. Moreover, equine papillomavirus infection results in substantial expense (many millions of dollars yearly) to the equine industry. Therefore, an equine papillomavirus vaccine produced according to the invention should possess tremendous potential for protecting equines against equine papillomavirus infection and squamous cell carcinoma caused thereby. As with the afore-described papillomavirus vaccines, this vaccine will comprise a prophylactically effective amount of recombinant equine papillomavirus L1 proteins or fragments which exhibit the conformation of L1 proteins expressed by native equine papillomavirus virions.

Based on the high level of sequence similarities between the L1 sequences of different papillomaviruses, the equine papillomavirus L1 sequence can readily be cloned and expressed in a suitable expression system, e.g., baculovirus.

For expression in an appropriate expression system, the L1 gene is operably linked into an expression vector and introduced into a host cell to enable the expression of the L1 protein by that cell. The gene with the appropriate regulatory regions will be provided in proper orientation and reading frame to allow for expression. Methods for gene construction are known in the art. See, in particular, *Molecular Cloning, A Laboratory Manual*, Sambrook et al, eds., Cold Spring Harbor Laboratory, Second Edition, Cold Spring Harbor, N.Y. (1989) and the references cited therein.

A wide variety of transcriptional and translational regulatory sequences may be employed. The signals may be derived from viral sources, where the regulatory signals are associated with a particular gene which has a high level of expression. That is, strong promoters, for example, of viral or mammalian sources, will be utilized. In this manner, the optimum conditions for carrying out the invention include the cloning of the L1 gene into an expression vector that will overexpress conformationally-dependent epitopes of the L1 protein in transfected or infected target cells.

The recombinant L1 protein is confirmed by reaction with antibodies or monoclonal antibodies which react or recognize conformational epitopes present on the intact virion. In this manner, the L1 protein can be verified as having the suitable conformation. Thus, other expression vectors and expression systems can be tested for use in the invention.

As discussed, it is essential that the expressed L1 protein be conformational, i.e., that it contain conformational epitopes that are necessary for a protective immunogenic response. This will typically be accomplished by expression of the entire L1 sequence of the particular papillomavirus, e.g., COPV or a human papillomavirus, e.g., HPV-6, HPV-11, HPV-16, HPV-18, among others. However, the invention also embraces expression of L1 DNA fragments, i.e., which do not comprise the entire L1 coding sequence but which upon expression still produce conformational L1 proteins, i.e., L1 proteins which contain conformational epitopes.

The specific L1 DNA fragments which results in the expression of conformational L1 proteins may be identified, e.g., by expressing different fragments of a particular L1 DNA, and ascertaining whether the resultant protein is conformational. This may be effected, e.g., by determining whether the particular L1 fragment reacts with or elicits the production of antibodies specific to conformational L1 epitopes.

To confirm that PV L1 DNA fragment encoding less than the entire L1 protein may be obtained which upon expression result in conformational L1 proteins, fragments of the COPV L1 open reading frame were expressed. In particular, fragments of the COPV L1 open reading frame were expressed which contained either a deletion in the amino-terminal or carboxy-terminal portion of the L1 sequence. It was found that the L1 protein containing the amino-terminal deletion expressed in a SV40 vector in COS cells apparently did not result in conformational L1 proteins (when tested with conformationally-dependent antibodies). By contrast, the L1 sequence which contained a deletion in the carboxy-terminal region when expressed in COS cells using the same SV40 vector system resulted in conformational L1 proteins (as demonstrated by binding to antibodies which recognize conformational epitopes). This carboxy-deletion consisted of deletion of the 26 amino acid fragment of the COPV L1 sequence, which was replaced by a 5 amino acid nuclear sequence of a nonstructural viral protein (large T protein) of SV40. The 26 amino acids of the COPV L1 sequence deleted include the nuclear signal sequences necessary for translocation of the native L1 protein into the cell nucleus. The particular nuclear signal sequence is not critical and is only necessary for transport into the nucleus. In this regard, many nuclear signal sequences are well known in the art. Thus, these results demonstrate that L1 fragments encompassing the carboxy terminus of the L1 protein are not necessary for reproducing conformational epitopes.

While only 26 amino acids of the carboxy-terminus were deleted, it is reasonable to assume that larger deletions will also result in conformational L1 proteins. As indicated, those deletions which are operable, i.e., which result in conformational L1 proteins, may be identified based on the reactivity of the resultant L1 fragments with conformational antibodies. This may be determined, e.g., by immunofluorescence or immunoprecipitation using conformational L1 antibodies.

Also, while only a carboxy-terminal deletion was demonstrated to yield conformational L1 proteins upon expression, it is believed that other deletions may also result in conformational L1 proteins. For example, internal deletions may also result in the formation of conformational L1 proteins. Also, it is expected that substitution mutations may be identified which result in conformational L1 proteins. Such substitutions may potentially be made in both the conserved and hypervariable regions of the L1 protein.

Moreover, while only COPV L1 fragments (containing deletion of 26 carboxy-terminal amino acids) were demonstrated to yield conformational L1 proteins, it is reasonable to expect that similar results will be obtained with other PV L1 sequences, given their high level of homology. It is especially reasonable to assume that similar results will be observed with carboxy-terminal deletions of HPV L1 sequences given the substantial similarities between HPVs and COPV.

COPV and HPVs associated with human malignancy are highly similar. They exhibit similar genetic organization, viral structure, capsid protein sequences, and selectively infect a mucosal site of infection. Based on these similarities, carboxy-deletions of HPV L1 sequences should also result in conformational L1 proteins when expressed according to the invention. This can be confirmed by testing with conformational antibodies specific to the particular HPV L1 fragment being expressed.

Once the L1 protein of suitable conformation has been expressed, antibodies can be raised against the recombinant protein or antigenic fragments thereof. The antibodies of the present invention may be prepared using known techniques. Monoclonal antibodies are prepared using hybridoma technology as described by Kohler et al, *Nature,* 256:495 (1975); Kohler et al, *Eur. J. Immunol.,* 6:511 (1976); Kohler et al, *Eur. J. Immunol.,* 6:292 (1976); Hammerling et al, in: *Monoclonal Antibodies and T-Cell Hybridomas*, Elsavier, N.Y., pages 563–681 (1981). Such antibodies produced by the methods of the invention are capable of protecting against PV infection.

The term "antibody" includes both polyclonal and monoclonal antibodies, as well as fragments thereof, such as, for example, Fv, Fab and $F(ab)_2$ fragments which are capable of binding antigen or hapten. Such fragments are typically produced by proteolytic cleavage, such as papain, to produce Fab fragments or pepsin to produce $F(ab)_2$ fragments. Alternatively, hapten-binding fragments can be produced through the application of recombinant DNA technology or through synthetic chemistry.

As indicated, both polyclonal and monoclonal antibodies may be employed in accordance with the present invention. Of special interest to the present invention are antibodies which are produced in humans or are "humanized" (i.e., non-immunogenic in a human) by recombinant or other technology. Humanized antibodies may be produced, for example, by placing an immunogenic portion of an antibody with a corresponding, but non-immunogenic portion, chimeric antibodies. See, for example, Robinson et al, International Patent Publication PCT/US86/02269; Akira et al, European Patent Application 184,187; Taniguchi, M. European Patent Application 171,496; Morrison et al, European Patent Application 173,494; Neuberger et al, PCT Application W086/01533; Cabilly et al, European Patent Application 125,023; Better et al, *Science,* 240:1041–1043 (1988); Liu et al, *PNAS,* 84:3439–3443 (1987); Liu et al, *J. Immunol.,* 139:3521–3526 (1987); Sun et al, *PNAS,* 84:214–218 (1987); Nishimura et al, *Cancer Research,* 47:999–1005 (1987); Wood et al, *Nature,* 314:446–449 (1985); and Shaw et al, *J. National Cancer Inst.,* 80:1553–1559 (1988). General reviews of "humanized" chimeric antibodies are provided by Morrison, S. L., *Science,* 229:1202–1207 (1985) and by Oi et al, *BioTechniques,* 4:214 (1986).

The antibodies, or antibody fragments, of the present invention can be utilized to detect, diagnose, serotype, and treat papillomavirus infection. In this manner, the antibodies or antibody fragments are particularly suited for use in immunoassays.

Antibodies, or fragments thereof, may be labeled using any of a variety of labels and methods of labeling. Examples of types of labels which can be used in the present invention include, but are not limited to, enzyme labels, radioisotopic labels, non-radioactive isotopic labels, fluorescent labels, toxin labels, and chemiluminescent labels.

Examples of suitable enzyme labels include malate hydrogenase, staphylococcal nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, acetylcholine esterase, etc.

Examples of suitable radioisotopic labels include $^{3}H$, $^{125}I$ , $^{131}I$, $^{32}P$, $^{35}S$, $^{14}C$, $^{51}Cr$, $^{57}To$, $^{58}Co$, $^{59}Fe$, $^{75}Se$, $^{152}Eu$, $^{90}Y$, $^{67}Cu$, $^{217}Ci$, $^{211}At$, $^{212}Pb$, $^{47}Sc$, and $^{109}Pd$.

Examples of suitable fluorescent labels include a $^{152}Eu$ label, a fluorescein label, an isothiocyanate label, a rhodamine label, a phycoerythrin label, a phycocyanin label, and allophycocyanin label, an o-phthaldehyde label, an fluorescamine label, etc.

Examples of suitable toxin labels include diphtheria toxin, ricin, and cholera toxin. Examples of chemiluminescent labels include a luminal label, an isoluminal label, an aromatic acridinium ester label, and imidazole label, and acridinium salt label, an oxalate ester label, a luciferin label, a luciferase label, an aequorin label, etc.

Those of ordinary skill in the art will know of other suitable labels which may be employed in accordance with the present invention. The binding of these labels to antibodies or fragments thereof can be accomplished using standard techniques commonly known to those of ordinary skill in the art. Typical techniques are described by Kennedy et al, *Clin. Chim. Acta,* 70:1–31 (1976), and Schurs et al,

*Clin. Chim. Acta,* 81:1–40 (1977). Coupling techniques mentioned in the latter are the glutaraldehyde method, the periodate method, the dimaleimide method, the m-maleimidobenzyl-N-hydroxy-succinimide ester method, all these methods incorporated by reference herein.

The detection of the antibodies (or fragments of antibodies) of the present invention may be improved through the use of carriers. Well-known carriers include glass, polystyrene, polypropylene, polyethylene, dextran, nylon, amylases, natural and modified celluloses, polyacrylamides, agaroses and magnetite. The nature of the carrier can be either soluble to some extent or insoluble for the purposes of the present invention. Those skilled in the art will note many other suitable carriers for binding monoclonal antibody, or will be able to ascertain the same by use of routine experimentation.

By raising antibodies against L1 proteins which mimic the antigenicity of papillomavirus virions, the antibodies raised against such recombinant proteins are neutralizing and protective antibodies. The antibodies are able to prevent subsequent infection of the same type of papillomaviruses from which the L1 protein was derived. That is, if a recombinant L1 protein from papillomavirus type 16 is utilized to raise antibodies, these antibodies will protect against subsequent infection of papillomavirus type 16. Thus, the method of the present invention provides for the prevention, treatment or detection of any HPV type.

The antibodies of the invention can be utilized to determine HPV types by serotyping as set forth in Jenson et al, *J. Cutan. Pathol.,* 16:54–59 (1989). Determining the HPV type may be clinically important for determining the putative biological potential of some productively infected HPV-associated lesions, particularly benign and low-grade premalignant anogenital tract lesions. Thus, the present invention makes it possible to treat and prevent infection of any type of PV from which the L1 gene can be obtained and neutralizing antibodies obtained.

The invention also provides for pharmaceutical compositions as the antibodies can also be utilized to treat papillomavirus infections in mammals. The antibodies or monoclonal antibodies can be used in pharmaceutical compositions to target drug therapies to sites of PV infection. In this manner, the drugs or compounds of interest are linked to the antibody to allow for targeting of the drugs or compounds. Methods are available for linking antibodies to drugs or compounds. See, for example, EP 0,146,050; EP 0,187,658; and U.S. Pat. Nos. 4,673,573; 4,368,149; 4,671, 958 and 4,545,988.

Such drug therapies include antiviral agents, toxic agents and photoactivatable compounds, such as coumarin, psoralen, phthalocyanimes, methylene blue, eosin, tetracycline, chlorophylls, porphyrins and the like. Such groups can be attached to the antibodies by appropriate linking groups. Antibody conjugates containing a photoactivatable compound are administered followed by irradiation of the target cells.

The antibody or antibody conjugates of the present invention can be formulated according to known methods to prepare pharmaceutically useful compositions such as by admixture with a pharmaceutically acceptable carrier vehicle. Suitable vehicles and their formulation are described, for example, in Remington's Pharmaceutical Sciences (16th Ed., Osol, A.Ed., Mack Easton, Pa. (1980)). To form a pharmaceutically acceptable composition suitable for effective administration, such compositions will contain an effective amount of antibody, either alone, or with a suitable amount of carrier vehicle.

The therapeutic or diagnostic compositions of the invention will be administered to an individual in therapeutically effective amounts. That is, in an amount sufficient to diagnose or treat PV infection. The effective amount will vary according to the weight, sex, age and medical history of the individual. Other factors include, the severity of the patient's condition, the type of PV, mode of administration, and the like. Generally, the compositions will be administered in dosages ranging from about 0.01 to about 2 picomoles/ml, more generally about 0.001 to about 20 picomoles/ml.

The pharmaceutically prepared compositions may be provided to a patient by any means known in the art including oral, intranasal, subcutaneous, intramuscular, intravenous, intraarterial, parenteral, etc.

Another aspect of the present invention involves the development of PV type-specific vaccines. The vaccines of the invention are those that contain the necessary antigenic determinants to induce formation of neutralizing antibodies in the host; possess high immunogenic potential; are safe enough to be administered without danger of clinical infection; devoid of toxic side-effects; suitable for administration by an effective route, for example, oral, intranasal, topical or parenteral; mimics the circumstances of natural infection; stable under conditions of long-term storage; and, compatible with the usual inert vaccine carriers.

The vaccines of the present invention include the conformationally correct recombinant L1 proteins or fragments thereof which provide the conformational epitopes present on the intact virions. Such amino acid sequences of the L1 protein comprise the antigenic component of the vaccine. It may be necessary or preferable to covalently link the antigen to an immunogenic carrier, i.e., bovine serum albumin or keyhole limpet hemocyanin. The vaccines of the invention may be administered to any mammal susceptible to infection with the papillomavirus. Human and non-animal mammals may benefit as hosts.

Administration of the vaccines may be parenteral, but preferably oral or intranasal, depending upon the natural route of infection. The dosage administered may be dependent upon the age, health, weight, kind of concurrent treatment, if any, and nature and type of the papillomavirus. The vaccine may be employed in dosage form such as capsules, liquid solutions, suspensions, or elixirs, for oral administration, or sterile liquid formulations such as solutions or suspensions for parenteral or intranasal use. An inert, immunologically acceptable carrier is preferably used, such as saline or phosphate-buffered saline.

The vaccines will be administered in therapeutically effective amounts. That is, in amounts sufficient to produce a protective immunological response. Generally, the vaccines will be administered in dosages ranging from about 0.1 mg protein to about 20 mg protein, more generally about 0.01 mg to about 100 mg protein. A single or multiple dosages can be administered.

The method of the present invention makes possible the preparation of subviral vaccines for preventing papillomavirus infection. Further, by following the methods of the invention, vaccines for any immunogenic type of specific papillomavirus can be made.

As more than one PV type may be associated with PV infections, the vaccines may comprise L1 antigenic amino acids from more than one type of PV. For example, as HPV 16 and 18 are associated with cervical carcinomas, a vaccine for cervical neoplasias may comprise L1 protein of HPV 16; of HPV 18; or both HPV 16 and 18.

In fact, a variety of neoplasias are known to be associated with PV infections. For example, HPVs 3a and 10 have been associated with flat warts. A number of HPV types have been reported to be associated with epidermodysplasia verruciformis (EV) including HPVs 3a, 5, 8, 9, 10, and 12. HPVs 1, 2, 4, and 7 have been reported to be associated with cutaneous warts and HPVs 6b, 11a, 13, and 16 are associated with lesions of the mucus membranes. See, for example, Kremsdorf et al, *J. Virol.*, 52: 1013–1018 (1984); Beaudenon et al, *Nature*, 321:246–249 (1986); Heilman et al, *J. Virol.*, 36:395–407 (1980); and DeVilliers et al, *J. Virol.*, 40:932–935 (1981). Thus, vaccine formulations may comprise a mixture of L1 proteins from different PV types depending upon the desired protection.

In the same manner, the pharmaceutical compositions may contain a mixture of antibodies to different PV types.

As indicated, the L1 protein of the invention can be utilized for serotyping.

That is, monoclonal antibodies capable of reacting with conformationally correct L1 protein can be produced which can be used to serotype PV. In this manner, tissue or serum can be obtained from a patient and analyzed for the ability to immunoprecipitate such antibodies In a broader sense, the antibodies can be used for serological screening. In this manner, populations of individuals can be tested for the ability to immunoprecipitate conformationally correct antibodies. Specific HPV type antibody responses can be determined.

The invention lends itself to the formulation of kits, particularly for the detection and serotyping of HPV. Such a kit would comprise a carrier being compartmentalized to receive in close confinement one or more containers, each container having antibodies for a particular HPV type or a mixture of antibodies for a variety of known HPV types. Other containers may contain means for detection such as enzyme substrates, labelled antigen/anti-antibody and the like.

For serological testing, the kits will comprise the conformationally correct recombinant L1 protein. Such a kit could also be utilized for vaccines.

While the present invention is generally directed to producing by recombinant method conformationally correct papillomavirus L1 proteins of any human or animal papillomavirus, as well the use of such proteins as vaccines, and or diagnosis and serotyping, in the preferred embodiments the recombinantly produced, conformationally correct L1 proteins will comprise human papillomavirus L1 proteins, canine oral papillomavirus (COPV) L1 proteins or equine papillomavirus L1 proteins.

As discussed supra, the canine oral papillomavirus (COPV) animal model offers a unique and highly relevant is animal model for the development of human canine papillomavirus vaccines. Moreover, unlike the available rabbit and bovine papillomavirus models, COPV is tropic for mucous membranes and is assayable for infectivity under natural conditions of exposure. Using a beagle colony which exhibits a high, natural incidence of oral papillomas, the present inventors have demonstrated that these tumors express viral capsid proteins and contain intact viruses, which are preventable by immunization with virus-containing tumor extracts. Moreover, as described in greater detail infra, it has been demonstrated that administration of formalin-inactivated COPV or recombinant COPV conformational L1 proteins confers complete protection upon challenge with the virus.

As discussed, infection of the oral mucous by COPV results in the induction of well-differentiated, benign, squamous cell tumors (warts). These lesions contain episomal DNAs which have been cloned separately by two research groups (Sundberg et al, *Amer. J. Vet. Res.*, 47:1142–1144 (1986); Bregman et al, *Vet Patriol.*, 24:477–487, (1987). The COPV genome is slightly larger (8.2 Kb) than most other papillomavirus genomes (8.0 Kb) but the two isolates characterized to date exhibit identical restriction enzyme cleavage patterns. Inoculation of beagles with wart extracts, similar to the bovine and rabbit models, induces immunity to subsequent reinfection [unpublished results]. Unfortunately, in a small proportion of vaccinated animals, squamous cell carcinoma develops at the site of injection (Bregman et al, *Vet Pathol.*, 24:477–487 (1987)). This presumably results from the neoplastic transformation of cutaneous keratinocytes by COPV which become entrapped in the needle during injection.

Sequencing results have demonstrated that the L1 gene of COPV is highly homologous to the L1 gene of HPV-1. Moreover, this virus possesses several critical characteristics which render it an ideal animal model for the "malignancy-associated" human papillomaviruses which distinguish it from the current rabbit and bovine models.

In particular, COPV, in contrast to CRPV, BPV-1 and BPV-2, infects and induces tumors at mucosal sites. This site mimics that for the mucosotrophic HPV-16 and HPV-18 which infect genital mucosa which are associated with cervical carcinoma. COPV has been isolated from genital mucous but not from cutaneous sites. Thus, COPV provides an ideal animal model for study of mucosotropic papillomaviruses which infect genital mucosa, and for screening and design of vaccines for providing immunity against such mucosotrophic papillomaviruses. This is extremely beneficial because of the fact that some mucosal HPVs, e.g., HPV-16 and HPV-18 are associated with cervical carcinoma.

Moreover, vaccines designed to prevent mucosal lesions may have specific requirements for generating IgA responses and for initiating an immune response in a specific subset of B lymphocytes.

Additionally, unlike the currently available CRPV and BPV models, COPV exhibits a high endogenous infection in a specific beagle colony. Thus, it is possible to escalate the efficacy of vaccines for preventing this naturally occurring infection. By contrast, the bovine and rabbit models require artificial means of infection (cutaneous abrasion) which may not necessarily reflect the natural mechanism of mucosal infections. Therefore, the beagle/COPV model should permit enhanced evaluation of the efficacy of putative vaccines against mucosal papillomaviruses such as COPV, HPV-16 and HPV-18 since it will better mimic in-vivo conditions than the CRPV and BPV models.

Further, carcinomas can develop at the site of benign tumors in a small percentage of animals as well as at the site of injection of crude "live" wart extracts. The limited conversion of benign lesions into carcinomas is also observed in human infected by mucosal papillomaviruses (HPV-16 and HPV-18) and represent the most serious consequence of HPV infection. Malignant conversion does not occur with cutaneous BPV, but does occur with CRPV in domestic rabbits.

This is highly significant because an effective vaccine against human papillomaviruses cell potentially reduce the incidence of human cervical dysplasia and carcinoma by 90–95%. However, due to the species specificity of these viruses, there are no animals into which HPV may be introduced to evaluate such vaccines. Moreover, because there are currently no tissue culture methods for propagating the virus, thereby eliminating the ability to assay viral neutralization in vitro. The only viable mechanisms for developing an HPV vaccine are to use prototype animal papillomaviruses which closely mimic the human disease process.

Thus, in light of the above, COPV should afford significant advantages over available rabbit and bovine papillomavirus animal models. Further, because the capsid proteins of COPV are closely related to HPV and since the biology of COPV closely mimics that of certain human papillomaviruses, e.g., HPV-16 and HPV-18, the identification of an effective COPV vaccine will yield direct benefits both because of potential veterinary applications, and more importantly to the development of vaccines against HPV's associated with cervical carcinoma.

Therefore, the present invention provides for the production of conformationally correct COPV L1 proteins, and the use of such COPV L1 proteins as vaccines against COPV, as well as the use thereof as an in vivo animal model for the development of human papillomavirus vaccines.

The present inventors studied the ability of conformationally correct COPV L1 proteins to afford immunity against COPV challenge in a beagle colony which exhibits a natural high incidence of oral warts formation as a consequence of viral infection. However, it is expected that the present invention will be applicable with any canine which is naturally susceptible to COPV infection.

Additionally, the present COPV/canine animal model further provides a means for delineating the role of antibodies against conformational epitopes of the COPV L1 proteins, as well as the L2 protein, in providing for resistance against COPV infection upon challenge with COPV.

This may be effected by injection of COPV wart extract (known to contain COPV viral particles) into susceptible animals. Also, the L1 and the L2 genes of COPV may be expressed in expression vectors which provide for the production of conformationally correct L1 and L2 proteins. As discussed supra, this will preferably be effected using eukaryotic expression vectors, e.g., mammalian, insect or yeast cells, e.g., Saccharomyces. Particularly preferred host cells for expression of COPV L1 proteins include by way of example COS cells and recombinant baculovirus infected Sf9 cells which produce L1 proteins which self-assemble into virus-like particles which antigenically mimic the intact COPV virion.

The conformationally correct COPV L1 and/or L2 proteins will be used to screen immune animal sera for the presence of L1 and L2 specific antibodies as well as to induce immunity in susceptible animals. The present invention further facilitates the identification of optimal conditions for inducing immunity in susceptible animals against COPV infection. Additionally, given the similarities between COPV and HPVs, the present invention further enables the identification of optimal conditions for inducing immunity against HPVs, in particular HPV-16 and HPV-18.

The ability of COPV L1 and L2 antibodies to inhibit COPV-induced tumors can be evaluated using virions purified from wart tissue or from other sources such as viral-producing tumors grown in nude mice.

Also, the conformationally correct COPV L1 and L2 proteins produced according to the invention can be used to generate monoclonal antibodies which may be used as therapeutics for providing passive immunization against COPV or as diagnostic agents. Further, monoclonal antibodies generated against intact virions may be used to define the molecular location of conformational, neutralizing epitopes on the COPV L1 and L2 proteins. Moreover, due to the structural and immunogenic similarity between COPV and HPVs, these antibodies may further have potential applicability in the development of human papillomavirus vaccines and diagnostic agents.

Immunization studies with COPV conformationally correct L1 and L2 proteins produced according to the present invention should enable the precise identification of specific dosages, carriers, adjuvants, frequency of administration and route of administration which provide for optimal immunity against COPV infection and possibly against HPV infection given the substantial similarities of COPV and HPV5. Immunity will be determined by studying vaccinated animals for the spontaneous appearance of oral warts.

Additionally, at selected times pre- and post-vaccination, animals will be evaluated for the presence of IgG, IgM and IgA antibodies which react with intact virus, or with L1 or L2 proteins. The temporal production of antibodies, as well as the ability of these antibodies to inhibit COPV infection will also be tested. In this regard, the present inventors have determined that injection of purified virus-like particles, with or without adjuvant, by systemic intradermal route of administration protects beagles from intraviral challenge with infectious COPV. Also, serum produced against intact virions were found to develop rapidly and to remain high in vaccinated beagles. By contrast, control, naive beagles were highly susceptible to challenge administered by the same route.

It has further been demonstrated by the present inventors that immunoglobulin fractions from vaccinated beagles which are passively transferred into weaning recipient beagles confer complete protection against COPV challenge. This provides additional evidence that the subject conformationally correct L1 and L2 proteins confer immunity against COPV by inducing a humoral (antibody) response against conformational epitopes contained on the L1 and L2 proteins.

Having now generally described the invention, the following examples are offered by way of illustration and not intended to be limiting unless otherwise specified.

Experimental

EXAMPLE 1

Materials and Methods (for Examples 1–3) Animals

Female, athymic (nu/nu) mice were purchased from Harlan Sprague Dawley, Madison, Wis., and used for xenograft transplants when 6 to 8 weeks old.
Virus BPV-1 was purified from experimentally-induced bovine cutaneous fibropapillomas as described by Lancaster, W. D. and Olson, D., Demonstration of two distinct classes of bovine papillomavirus, *Virology*, 89:372–279 (1978) (1978). The virus was stored at −80° C. until used.
Antibodies All serum samples were heat-inactivated at 56° C. for 30 min. Each antibody preparation was evaluated for reactivity with intact and disrupted BPV-1 particles (Table I) before testing for neutralization of BPV-1 induced transformation of C127 cells and xenografts.

Bovine polyclonal antibodies. Bovine sera were obtained from calves either vaccinated with BPV-1 L1 fusion proteins or experimentally-infected with BPV-1.

Holstein X Angus calves were immunized with different formulations of a recombinant BPV-1 L1::B-galactosidase vaccine (Jin, X. W., Cowsert, L., Marshall D., Reed, D., Pilacinski, W., Lim, L. and Jenson, A. B., Bovine serological response to a recombinant BPV-1 major capsid protein vaccine, *Intervirology,* 31:345–354 (1990)). The cloned L1 gene begins 76 bp down stream from the start codon of the L1 open reading frame at nucleotide 5686 and is terminally fused to the *E. coli* B-galactosidase gene (Pilacinski, W. P., Glassman, D. L., Richard, A. K. Sadowski, P. L. and Alan, K. R., Cloning and expression in *Escherichia coli* of the bovine papillomavirus L1 and L2 open reading frames, *Bio/Technol.,* 2:356–360 (1984)). Calves were vaccinated on days 0 to 21, and challenged by intradermal inoculation of 2 sites with 1010 BPV-1 particles on day 56 (Jin, X. W., Cowsert, L., Marshall D., Reed, D., Pilacinski, W., Lim, L. and Jenson, A. B., Bovine serological response to a recombinant BPV-1 major capsid protein vaccine, *Intervirology,* 31:345–354 (1990)). The calves were bled on days 3 (designated as pre-bleed), 55 (bleed 1) and 104 (bleed 2) days of the trial and the sera tested for reactivity with intact and disrupted BPV-1 particles by ELISA. Although 90% and 58% of calves developed antibody responses to internal and external BPV-1 capsid epitopes respectively, all calves developed fibromas.

Two steer (926 and 921), acquired as calves from a sequestered herd of cattle without prior exposure to BPV-1 or BPV-2, were inoculated at multiple sites with finely ground homogenates of BPV-1 induced fibropapillomas. Fibropapillomas developed in the scarified sites and persisted for varying lengths of time before undergoing spontaneous regression. The sera used in this experiment were collected during the earliest signs of fibropapilloma regression in both animals.

Rabbit polyclonal antibodies. Rabbit anti-sera were prepared by inoculation with either intact BPV-1 or BPV-2 virions, or denatured BPV-1 particles and then bled 2 weeks after the final immunization (Jenson, A. B. Rosenthal, J. D., Olson, C., Pass, F. W., Lancaster W. D. and Shah, K., Immunologic relatedness of papillomaviruses from different species, *J. Nat. Cancer Inst.,* 64:495–500 (1980), Jenson, A. B., Kurman, R. J. and Lancaster, W. D., Detection of papillomavirus common antigens in lesions of the skin and mucosa, *Clinics In Dermatol.,* 3:56–63 (1985); Cowsert, L. M., Lake, P. and Jenson, A. B., Topographical and conformational epitopes of bovine papillomavirus type 1 defined by monoclonal antibodies, *J. Nat. Cancer Inst.,* 79:1053–1057 (1987)).

Murine monoclonal antibodies. Two murine MAbs, 13D6 and JG, were also used to test for neutralization. 13D6 recognizes conformational epitopes on BPV-1, BPV-2 and deer papillomavirus (DPV) intact particles (Cowsert, L. M., Lake, P. and Jenson, A. B., Topographical and conformational epitopes of bovine papillomavirus type 1 defined by monoclonal antibodies, *J. Nat. Cancer Inst.,* 79:1053–1057 (1987)), whereas JG recognizes a BPV-1 type-specific linear epitope internal to the capsid (data not shown).

TABLE I

ELISA REACTIVITY OF BOVINE, RABBIT AND HUMAN SERA AND MURINE MAbs WITH INTACT AND DISRUPTED BPV-1 PARTICLES

| Serum[1] or MAb samples | BPV-1 particles | |
|---|---|---|
| | Intact | Disrupted |
| Vaccinated calves[2] | | |
| 163 | | |
| Pre-bleed | 0.002 | 0.016 |

TABLE I-continued

ELISA REACTIVITY OF BOVINE, RABBIT AND HUMAN SERA AND MURINE MAbs WITH INTACT AND DISRUPTED BPV-1 PARTICLES

| Serum[1] or MAb samples | BPV-1 particles | |
|---|---|---|
| | Intact | Disrupted |
| 1 | 0.041 | 0.925 |
| 2 | 0.312 | 1.472 |
| 173 | | |
| Pre-bleed | 0.036 | 0.066 |
| 1 | 0.101 | 1.222 |
| 2 | 0.182 | 1.249 |
| Rabbit[3] | | |
| NRS | 0.065 | 0.073 |
| BPV-1 | 1.454 | 0.095 |
| BPV-2 | 1.621 | 0.085 |
| BPV-1 (SDS) | 0.319 | 1.358 |
| MAbs | | |
| 13D6 | 0.629 | 0.004 |
| JG | 0.004 | 0.423 |
| Hyperimmune steers[4] | | |
| 926 | 0.296 | 0.033 |
| 921 | 0.397 | 0.202 |
| Human | | |
| 1 | 0.964 | 0.036 |
| 2 | 0.554 | 0.247 |

[1]RBPV-1 and RBPV-2 were diluted 1/2000; all other samples were diluted 1/50.
[2]Pre, pre-bleed sera from calves 163 and 173; 1, sera of calves 163 and 173 at the time of challenge with BPV-1 virions; 2, sera of calves 163 and 173 at end of the vaccine trial.
[3]NRS, normal rabbit serum; BPV-1 (SDS) rabbit serum prepared against SDS-disrupted BPV-1.
[4]Steers (926 and 921), serum of steer inoculated at 24 different cutaneous sites with BPV-1 homogenates.

Neutralization assays

Two assays (xenografts in athymic mice and murine C127 cells cultures) for detecting antibody-mediated neutralization of infectious PV virions were compared for specificity.

Xenograft assay. To assay for neutralization of BPV-1 infectivity, a 1:10 dilution of polyclonal anti-sera in PBS was added to aliquots of infectious BPV-1 in PBS and incubated for 1 hr at 37° C. BPV-1 in PBS alone was included as a positive control for infectivity. Bovine fetal skin chips (5 to 10×2-×2-mm pieces) were added to each dilution and incubated for 1 hr at 37° C.

The chips were transplanted under the renal capsule of athymic mice and cyst size (in mm) and morphology of its lining epithelium was determined after 60 days. Cyst sizes were calculated as geometric mean diameters (BMDs) by calculating the cubic root of the length×width×height of cysts in mm.

Statistical analysis was accomplished by determining the means of the GMDs of cysts and fibropapillomas for each anti-serum and was compared with those for untreated controls by using the Student's t-test.

C127 cells assay. Murine C127 cells were obtained from ATCC, Rockville, Md., and grown as described by (Dvoretzky, I., Shober, R., Chattopadhy, S. K. and Lowy, D. R., A quantitative in vitro focus-forming assay for bovine Papillomavirus, *Virology,* 103:369–375 (1980)). The neutralization assays were carried out in Petri dishes (100 mm). C127 cells were seeded at approximately $10^5$ to $5 \times 10^5$ cells, which were allowed to become 75 to 80% confluent, BPV-1 virions ($10^3$ focus-forming units [FFU]) were then incubated with either 0.5 ml DMEM as a positive control for infectivity or an equal volume of the MAb or polyclonal antiserum (diluted 1:5) at 37° C. for 1 hr prior to inoculation of C127 cells. After 1½ hrs adsorption. 10% FBS supplemented MEM was added to each dish. The medium was replenished the next day and then 3 times each week for 17 to 19 days, at which time the dishes were fixed and stained 0.1% methylene blue in methanol to count the number of FF per dish. Controls included fetal calf sera and serum from a steer that had no history of fibropapillomas.

Results

The specificity of 2 different assay systems, xenografts and C127 cells, for measuring the neutralization of BPV-1 infection were compared using selected animal sera and murine MAbs. The sera and MAbs tested were: (1) sera from rabbits and cattle immunized and/or infected with intact BPV-1 and BPV-2 virions (the immune systems were exposed to both conformational and linear BP-1 capsid surface epitopes); (2) sera from rabbits and cattle immunized with denatured BPV-1 virions and L1 fusion proteins respectively (the immune systems were exposed to denatured/linear BPV-1 capsid epitopes); (3) selected sera from humans that reacted with intact BPV-1; and (4) MAbs that define BPV-1 conformational surface epitopes and epitopes that are internal to the BPV-1 capsid.

Epitope topography

The sera evaluated in our study were tested initially for reactivity with both intact and disrupted BPV-1 capsids, thus defining the topographical location of the corresponding epitopes as either external or internal to the BPV-1 capsid as previously described (Cowsert, L. M., Lake, P. and Jenson, A. B., Topographical and conformational epitopes of bovine papillomavirus type 1 defined by monoclonal antibodies, *J. Nat. Cancer Inst.*, 79:1053–1057 (1987)). (Table I).

Rabbit sera produced against intact BPV-1 or BPV-2 virions and sera from steers inoculated at multiple sites with infectious homogenates of BPV-1 induced fibropapillomas as well as MAb 13D6 reacted primarily with intact virions. The two human sera selected for this study reacted primarily with intact BPV-1 particles.

Rabbit serum prepared against SDS-disrupted BPV-1 viral particles, and sera (bleed 2) from calves 163 and 173 at the end of the vaccine trial, 48 days after challenge with BPV-1 virions, reacted with both intact and disrupted viral particles. Calf 163 serum (bleed 1), immediately prior to challenge with infectious BPV-1 virions, reacted only with disrupted BPV-1 particles. MAb JG reacted only with disrupted BPV-1 virions.

Pre-bleed/normal rabbit and bovine sera (calves 163 and 173 did not react either with intact or with disrupted BPV-1 virions by ELISA.

Neutralization assays

Two different assays were compared for neutralization of BPV-1 infectivity by the hyperimmune sera and MAbs: (i) xenografts in athymic mice, and (ii) C127 cell cultures.

Xenograft neutralization assay. Polyclonal antisera (non-absorbed) as well as negative control sera were tested for the neutralization of BPV-1 infectivity of bovine fetal skin transplanted beneath the renal capsule of athymic mice. Effective neutralization was determined by comparing cyst size and microscopic morphology (Table II).

Bovine fetal skin chips were incubated with BPV-1 which had been preincubated for 1 hr with dilutions of the various polyclonal antisera. The chips were grafted sub-renally in athymic mice, and average geometric mean diameters of cyst sizes were determined 60 days later (Table II). A large and significant reduction in cyst size was obtained for the sera from 2 rabbits inoculated with intact BPV-1 or BPV-2 and both steer polyclonal anti-sera collected from animals with regressing BPV-1 -induced fibropapillomas. Neither polyclonal anti-serum from the rabbit inoculated with denatured BPV-1 particles nor pre-bleed, challenge or post-challenge bovine sera from the recombinant vaccination study in calves and a significant effect on cyst size at the dilution tested. Human sera and MAbs reactive with intact BPV-1 particles or linear epitopes of BPV-1 did not result in cyst-size reduction.

C127 cell neutralization assay. Pre-bleed rabbit and calf 163 and 173 sera, hyperimmune rabbit serum prepared against SDS-disrupted BPV-1 virions, both human sera, and calf sera (163 and 173) following vaccination but immediately prior to challenge with BPV-1 , did not neutralize FF of C127 cells by BPV-1 virions (Table III). However, rabbit sera produced by immunization with intact BPV-1 and BPV-2 had neutralizing titers of $10^6$ and $10^4$ respectively, and the hyperimmune steer sera had a neutralizing titer of $10^6$ (926) to $10^3$ (921). Calves 163 and 173 sera at the end of the vaccination trial had a neutralizing titer of less than $10^1$, probably because of exposure to infectious challenge virus, rather than a maturing immune response against the vaccine.

Neither fetal calf sera nor selected adult steer serum from non-immune animals inhibited FF in C127 cells.

TABLE II

CYST SIZE AND MORPHOLOGY OF BPV-1 INDUCED XENOGRAFTS DEVELOPING AFTER VARIOUS SERUM PRETREATMENTS OF INFECTIOUS BPV-1

| Serum or MAb samples[1] | Cyst size[2] (mean and SEM in mm) | Morphology[3] |
|---|---|---|
| Vaccinated calves | | |
| 163 | 5.8(0.9)[4] | 5/6/6 |
| Pre-bleed | 4.0(0.4) | 4/4/4 |
| 1 | 4.6(0.5)[4] | 5/6/6 |
| 2 | | |
| 173 | 6.7(0.8)[4] | 6/6/6 |
| Pre-bleed | 5.2(0.7)[4] | 6/6/6 |
| 1 | 5.3(0.6)[4] | 6/6/6 |
| 2 | | |
| Rabbit | | |
| NRS | 5.8(0.6)[4] | 8/8/8 |
| BPV-1 | 3.5 | 0/10/10 |
| BPV-2 | (0.2)[5,6] | 1/6/6 |
| BPV-1 (SDS) | 3.3 | 4/4/4 |
| | (0.5)[5,6] | |
| | 8.3 | |
| | (0.5)[4,5] | |
| MAbs | | |
| 13D6 | 4.4(0.6)[4] | 6/6/6 |
| JG | 5.3(0.7)[4] | 6/6/6 |
| Hyperimmune | | |
| steers | 3.0(0.6)[5] | 0/3/4 |
| 926 | 3.4(0.4)[5] | 0/6/6 |
| 921 | | |

TABLE II-continued

CYST SIZE AND MORPHOLOGY OF BPV-1 INDUCED
XENOGRAFTS DEVELOPING AFTER VARIOUS SERUM
PRETREATMENTS OF INFECTIOUS BPV-1

| Serum or MAb samples[1] | Cyst size[2] (mean and SEM in mm) | Morphology[3] |
|---|---|---|
| Human | | |
| 1 | 6.5(0.7)[4] | 6/6/6 |
| 2 | 5.0(0.4)[4] | 6/6/6 |

[1]Serum samples from various sources described in Table I.
[2]Cyst sizes were determined from geometric mean diameters.
[3]Number of cysts morphologically transformed/number of surviving cysts/number of grafts attempted.
[4]Mean cyst size significantly different ($p_5 < 0.05$) from BPV-1 -infected treatment group of (positive control for neutralization).
[5]Mean cyst size significantly different ($p < 0.05$) from rabbit anti-intact BPV-1 (previously used as positive control for BPV-1 xenograft neutralization studies).
[6]Mean cyst size significantly different ($p < 0.05$) from normal rabbit serum (previously used as negative control for BPV-1 xenograft neutralization studies).

TABLE III

NEUTRALIZATION OF BPV-1 INFECTION OF C127 CELLS BY
BOVINE, RABBIT AND HUMAN SERA AND MURINE MAbs

| Serum or MAb samples[1] | Neutralization titer[2] |
|---|---|
| Vaccinated calves | |
| 163 | |
| Pre-bleed | 0 |
| 1 | 0 |
| 2 | <10[1] |
| 173 | |
| Pre-bleed | 0 |
| 1 | 0 |
| 2 | <10[1] |
| Rabbit | |
| NRS | 0 |
| BPV-1 | 10[6] |
| BPV-2 | 10[2] |
| BPV-1 (SDS) | 0 |
| MAbs | |
| 13D6 | 0 |
| JG | 0 |
| Hyperimmune steers | |
| 926 | >10[6] |
| 921 | >10[3] |
| Human | |
| 1 | 0 |
| 2 | 0 |

[1]Identification of different sera and MAbs as in Table I.
[2]The neutralization titer is expressed as the reciprocal of the highest serum dilution required to neutralize focus formation of murine C127 cells by BPV-1 virions.

Discussion

The xenograft system has provided an effective model for the detection of antibody-mediated neutralization of productive PV infections, including BPV-1 (Christensen, N. and Kreider, J. W., Antibody-mediated neutralization in vitro of infectious papillomaviruses, *J. Virol.*, 64:3151–3156 (1990)). However neutralizing antibodies also prevent BPV-1 virions from inducing FF in non-productively infected murine C127 cells in culture (Dvoretzky, I., Shober, R., Chattopadhy, S. K. and Lowy, D. R., A quantitative in vitro focus-forming assay for bovine papillomavirus, *Virology*, 103:369–375 (1980)). To compare the specificity of the 2 methods, and to determine the epitopes responsible for neutralization, selected sera from cattle, rabbits and humans and murine MAbs were tested for neutralizing activity.

The papillomavirus genomes are encapsulated by L1 (major capsid) and L2 (minor capsid) proteins (Banks, L. Matlashewski, G. Pim, D., Churcher, M., Roberts, C. and Crawford, L., Expression of human papillomavirus type-6 and type-15 capsid proteins in bacteria and their antigenic characterization, *J. Gen. Virol.*, 69:3081–3089 (1987), Christensen, N. Kreider, J. W., Cladel, N. M. and Galloway, D. A., Immunological cross-reactivity to laboratory-produced HPV-11 virions of polysera raised against bacterially derived fusion proteins and synthetic peptides of HPV-6b and HPV-16 capsid proteins, *Virology*, 175:1–9 (1990), Cowsert, L. M., Lake, P. and Jenson, A. B., Topographical and conformational epitopes of bovine papillomavirus tyoe 1 defined by monoclonal antibodies, *J. Nat. Cancer Inst.*, 79:1053–1057 (1987), Cowsert, L. M., Pilacinski, W. P. and Jenson, A. B., Identification of the bovine papillomavirus L1 gene product using monoclonal antibodies, *Virology*, 165:613–615 (1988), Doobar, J. and Gallimore, P. H., Identification of proteins encoded by the L1 and L2 open reading frames of human papillomavirus 1a, *J. Virol.*, 61:2793–2799 (1987), Jin. X. W., Cowsert, L., Pilacinski, W. and Jenson, A. B., Identification of L2 open reading frame gene products of bovine papillomavirus type-1 by monoclonal antibodies, *J. Gen. Virol.*, 70:1133–1140 (1989), Komly, C. A., Breitburd, F., Croissant, O. and Streeck, R. E., The L2 open reading frame of human papillomavirus type-1a encodes a minor structural protein carrying type-specific antigens, *J. Virol.*, 60:813,816 (1986), Kreider, J. W., Howett, M. K., Wolfe, S. A., Barlett, G. L., Zaino, R. J., Sedlacek, T. V. and Mortel, R., Morphological transformation in vitro of human uterine cervix with papillomavirus from condylomata acuminata, *Nature* (Lond.), 317:639–640 (1985), Nakai, Y., Lancaster, W. D., Lim, L. Y. and Jenson, A. B., Monoclonal antibodies to genus- and tyoe-specific papillomavirus structural antigens, *Intervirology*, 25:30–37 (1986), Roseto, A., Pothier, P., Guillemin, M. C., Peries, J., Breitburd, F., Bonneaud, N. and Orth, G., Monoclonal antibody to the major capsid Protein of human papillomavirus type 1, *J. Gen. Virol.*, 65:1319–1324 (1984)), to form virions in the nuclei of terminally differentiating keratinocytes (Firzlaff, J. M., Kiviat, N. B., Beckmann, A. M., Jenison, A. and Galloway, D. A., Detection of human papillomavirus capsid antigens in various squamous epithelial lesions using antibodies directed against the L1 and L2 open reading frames, *Virology*, 164:467–477 (1988), Jenson, A. B., Rosenthal, J. D., Olson, C., Pass, F. W., Lancaster, W. D. and Shah, K., Immunologic relatedness of papillomaviruses from different species, *J. Nat. Cancer Inst.*, 64:495–500 (1980), Lim, P. S., Jenson, A. B., Cowsert, L., Nakai, Y., Lim, L. Y. and Sundberg, J., Distribution and specific identification of papillomavirus major capsid protein epitopes by immunocytochemistry and epitope scanning of synthetic peptides, *J. Infect. Dis.*, 162:1263–1269 (1990), Sandberg, J. P., Junge, R. E. and Lancaster, W. D., Immunoperoxidase localization of papillomaviruses in hyperplastic and neoplastic epithelial lesions of animals, *Amer. J. Vet. Res.*, 45:1441–1446 (1984)). The PV L1 capsid protein in contrast to the L2 protein, is highly conserved throughout the PV genus (Baker, C. C., Sequence analysis of papillomavirus genomes, In: N. P. Salzman and P. M. Howley (eds.), The papoviridae, Vol. 2, The papillomaviruses, pp. 321–385, Plenum, N.Y. (1987). However only type-specific and minimally cross-reactive linear and conformational epitopes of the L1 protein have been detected on the virion surface by MAbs, Cowsert, L. M., Lake, P. and Jenson, A. B., Topographical and conformational epitopes of bovine papillomavirus type 1 defined by monoclonal antibodies, *J. Nat. Cancer Inst.*, 79:1053–1057 (1987), Cowsert, L. M., Pilacinski, W. P. and Jenson, A. B., Identification of the bovine papillomavirus L1 gene product using monoclonal antibodies, *Virology*, 165:613–615 (1988) whereas type-specific linear epitopes of the L2 protein appear to be internal to the capsid (Jin. X. W., Cowsert, L., Pilacinski, W. and Jenson, A. B., Identification of L2 open reading frame gene products of bovine papillomavirus type-1 by monoclonal antibodies, *J. Gen. Virol.*, 70:1133–1140 (1989), Komly, C. A., Breitburd, F., Croissant, O. and Streeck, R. E., The L2 open reading frame of human papillomavirus type 1a encodes a minor structural protein carrying type-specific antigens, *J. Virol.*, 60:813,816 (1986), Tomita, Y., Shirasawa, H., Sekine, H. and Simizu, B., Expression of human papillomavirus type 6b L2 open reading frame in *Escherichia coli*::L2-β-galactosidase fusion proteins and their antigenic properties, *Virology*, 158:8–14 (1987)). In this study, only sera from rabbits immunized with either intact BPV-1 or BPV-2 virions and cattle infected with homogenates of productively infected fibropapillomas were capable of neutralizing infectivity of BPV-1 in both murine C127 cells and in the xenografts.

Although the neutralization assay in murine C127 cells may be more quantitative, primarily because the assay involves FF of single cells in a monolayer, it is no more specific than the xenograft system (Christensen, N. and Kreider, J. W., Antibody-mediated neutralization in vitro of infectious papillomaviruses. *J. Virol.* 64:3151–3156 (1990)), which is more analogous to neutralization of BPV-1 infection in the natural host by prior vaccination with intact virions (Jarrett, W. F. H., O'Neill, B. W., Gaukroger, J. M., Laird, H. M., Smith, K. T. and Campo, M. S., studies on vaccination against papillomaviruses: a comparison of purified virus, tumor extract and transformed cells in prophylactic vaccination. *Vet. Rec.* 126:449–452 (1990a), Jarrett, W. F. H., O'Neill, B. W., Gaukroger, J. M., Laird, H. M., Smith, K. T. and Campo, M. S., Studies on vaccination against papillomaviruses: the immunity after infection and vaccination with bovine papillomaviruses of different types. *Vet. Rec.* 126:473–475 (1990b)). Bovine sera from vaccinated calves almost 2 months after challenge with BPV-1 virions neutralized BPV-1 -induced FF of C127 cells, but did not prevent the development of fibropapillomas in the xenografts. Although both assays were accomplished using aliquots of the same sera, the differences in personnel, handling of specimens, conditions of infection and neutralization, which were performed at separate locations, could also explain the slight difference in results.

Rabbit and bovine sera that were prepared against either denatured BPV-1 capsids or recombinant BPV-1 L1 vaccine, respectively, did not neutralize BPV-1 infectivity in either neutralization assay. Since these sera only recognized continuous BPV-1 L1 epitopes, it was concluded that linearized BPV-1 surface epitopes were not capable of inducing neutralizing antibodies. Neutralizing activity in this study appears to be largely dependent upon conformational epitopes.

The 2-human sera that reacted with intact BPV-1 particles did not prevent BPV-1 -induced FF in C127 cells or transformation of bovine fetal skin in the xenograft model. This suggests that human sera either recognized a non-neutralizing mimeotope or defined BPV-1 conformational epitopes that are not associated with neutralization of BPV-1 infectivity. Nevertheless, these results support the concept that significant exposure to intact BPV-1 viral particles is necessary for the production of neutralizing antibodies (Jarrett, W. F. H., O'Neill, B. W., Gaukroger, J. M., Laird, H. M., Smith, K. T. and Campo, M. S., studies on vaccination against papillomaviruses: a comparison of purified virus, tumor extract and transformed cells in prophylactic vaccination. *Vet. Rec.* 126:449–452 (1990a), Jarrett, W. F. H., O'Neill, B. W., Gaukroger, J. M., Laird, H. M., Smith, K. T. and Campo, M. S., Studies on vaccination against papillomaviruses: the immunity after infection and vaccination with bovine papillomaviruses of different types. *Vet. Rec.* 126:473–475 (1990b)).

Our study reveals that neutralization of BPV-1 infectivity by serum antibodies can be measured by prevention of either FF in C127 cells or transformation of bovine fetal skin in the xenograft model. Since the results of the 2 assays were concordant, it is concluded that (1) neutralization of FF of C127 cells and transformation of bovine fetal skin in the xenografts both appear to be true indicators of the capacity of antibodies to neutralize BPV-1 infectivity, that is, the antibodies react with conformationally correct L1 protein; and (2) neutralization of FF by C127 cells can be used for studies of early BPV-1 virion-host cell interaction to define functional epitopes.

EXAMPLE 2

Expression of a prototype L1 protein (HPV-1) by the pSVL vector transfected into COS cells The L1 protein of HPV-1 was expressed because there exist several monoclonal antibodies against HPV-1 which react with conformational epitopes present on the intact virion. We reasoned that if we were successful in generating HPV-1 L1 protein with native conformation, these monoclonal antibodies might react with the isolated, expressed L1 protein. This would confirm the ability to produce L1 protein of suitable conformation to mimic that present on the intact virus particle. It is critical to generate an immune response against the conformational epitopes of the papillomaviruses in order to produce a neutralizing antibody.

The choice of vector was based upon several criteria. We desired to have expression vectors which produced high levels of capsid protein which would not only facilitate their use for vaccines but also potentially aid in achieving empty capsid formation in the nucleus. The pSVL vector and the baculovirus vectors both use very strong promoters and have been used extensively for expressing proteins. In addition, the pSVL vector contains an SV40 origin of replication and, when transfected in cos cells which express Large T antigen, replicates to high copy number. The replication of the input vector, combined with the strong activity of the viral promoter, results in extremely high levels of expressed protein. The cos cells are also permissive for the assembly of SV40 virions and might potentially facilitate the assembly of PV particles. The baculovirus system also offers the advantage that a larger percentage of cells can be induced to express protein (due to the use of infection rather than transfection techniques). While baculovirus is an insect virus and grows in insect cells (Sf9), these cells retain many of the eucaryotic mechanisms for processing of proteins (glycosylation and phosphorylation) which might be important for generating proteins of appropriate conformation.

Figure 1:
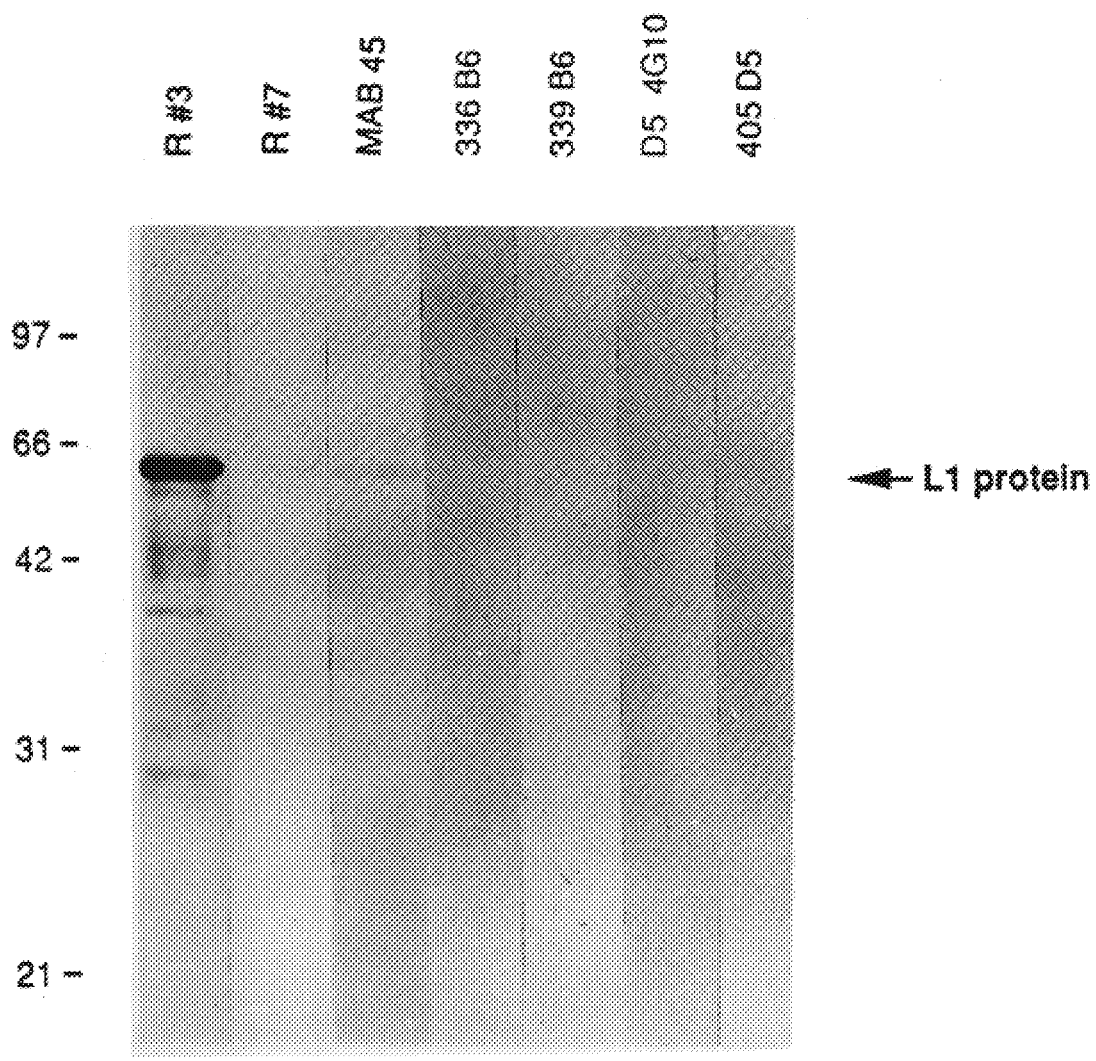
FIG. 1. Reactivity of rabbit polyclonal antisera and mouse monoclonal antibodies with SDS-disrupted HPV-1 as determined by immunoblot analysis.

The scheme for the cloning of the HPV-1 L1 protein into pSVL is shown in FIG. 1.

The expression of the HPV-1 L1 protein by pSVL was first assayed by immunofluorescence. COS cells were transfected with 1–10 μg of the plasmid shown in FIG. 1. After 48 hrs, the cells were fixed with cold methanol and then reacted with either non-immune mouse ascites (a), rabbit antiserum generated against SDS-disrupted BPV-1 (b), or mouse monoclonal antibody 405D5 which recognizes a type-specific, conformational epitope on HPV-1. A positive nuclear staining was seen with both antibodies and was absent from non-transfected cells. In addition, the L1 -expressing cells were also reactive with several additional monoclonal antibodies which specifically react with independent, conformational epitopes (data not shown). After transfection cos cells were then fixed with methanol and stained for reactivity with either control rabbit serum, Dako antiserum generated against SDS-disrupted BPV-1 virions, or mouse monoclonal antibody 405D5 which reacts specifically with HPV-1 virion conformational epitopes. Four additional conformation-specific monoclonal antibodies gave an identical immunofluorescence pattern and clearly indicate that the L1 protein synthesized in cos cells retains conformational epitopes. In addition, the L1 protein exhibits the anticipated intranuclear localization, reflecting the appropriate processing and translocation of this protein. This result demonstrates that the conformational epitope identified by 405D antibody is present entirely on the L1 protein (rather than L2 or a combination of L1/L2). Most importantly, the reactivity of L1 with this monoclonal antibody demonstrates the L1 protein has retained a conformational epitope identical to that found in its virion-associated state. Electron microscopy experiments are currently being performed to evaluate whether the L1 protein is assembling into empty viral particles. Thus, the pSVL vector is successful in producing HPV-1 L1 protein with a native conformation for generating antibody responses which react with intact virus particles.

The synthesis of the L1 protein was also determined by immunoprecipitation from transfected cos cells. At 48 hr post-transfection, the cos cells were metabolically labelled with S-35 methionine and cysteine for 4 hrs, extracted with RIPA buffer, and immunoprecipitated with rabbit antiserum generated against SDS-disrupted BPV-1 (Dako). We used this antibody for immunoprecipitations since the solubilization of L1 protein with denaturing detergents may abolish its recognition by the conformation-dependent L1 antibody described above. An SDS-PAGE of the immunoprecipitates indicates that the synthesized L1 protein is full-length (55 kD). This series of immunofluorescence and immunoprecipitation experiments demonstrates therefore that the pSVL vector will be able to generate L1 protein which will be suitable for inducing conformation-dependent antibodies.

EXAMPLE 3

Papillomavirus infections cause cutaneous warts and mucosal condylomata in a wide variety of vertebrate animals (Olson, C., in "The papovaviridae" (N. P. Salzman and P. M. Howley, Eds.), pp. 39–66, Plenum Press (1987)) and, in humans, are strongly associated with the development of cervical dysplasia and carcinoma (Jenson, A. B., and Lancaster, W. D., in "Papillomaviruses and human cancer" (H. Pfister, Ed.) pp. 11–43, CRC Press (1990)). Each papillomavirus type is highly species-specific and preferentially infects squamous epithelium at a restricted number of anatomic locations. Vegetative viral DNA replication occurs in the nucleus of terminally differentiated keratinocytes where the viral genome becomes encapsidated by the major (L1) and minor (L2) capsid proteins, forming virions 55 nm in diameter. Unfortunately, there are no tissue culture systems which permit sufficient keratinocyte differentiation to propagate papillomaviruses in vitro and this limitation has compromised the analysis of the late expression of the L1 and L2 genes as well as the characterization of the host immune response to their gene products.

Due to the etiologic role that human papillomaviruses (HPV's) play in some human malignancies, recent attention has been focused on the development of a recombinant capsid protein vaccine to reduce the incidence of HPV infection and its neoplastic sequelae. The first animal model for a potential vaccine utilized bovine papillomavirus type 1 (BPV-1). The L1 protein of BPV-1 was expressed in bacteria (Pilacinski, W. P., Glassmam, D. L., Krzyzek, R. A., Sadowski, P. L., and Robbins, A. K., *Biotechnology*, 2:356–360 (1984)) and used to immunize cattle against subsequent viral challenge (Pilacinski, W. P., Glassmam, D. L., Glassman, K. L., Read, D. E., Lum, M. A., Marshall, R. F., and Muscoplat, C. C., In "Papillomaviruses: molecular and clinical aspects" (T. R. Broker and P. M. Howley, Eds., pp. 257–271, Alan R. Liss, Inc., New York (1985)). However, since the expressed L1 protein apparently lacked native conformation (due to the insoluble, aggregate form of over-expressed, fusion proteins in bacteria), it did not induce antibodies which could either recognize or neutralize intact BPV-1 virions (Jin, X. W., Cowsert, L., Marshall, D., Reed, D., Pilacinski, W., Lim, L. Y., and Jenson, A. B., *Intervirology*, 31:345–354 (1990); and Ghim, S., Christensen, N. D., Kreider, J. W., and Jenson, A. B., Int. J. Cancer 49:285–289 (1991)).

The ability of antibodies to neutralize papillomaviruses appears to be related to their ability to react with type-specific, conformational epitopes on the virion surface (Ghim, S., Christensen, N. D., Kreider, J. W., and Jenson, A. B., *Int. J. Cancer*, 49:285–289 (1991); Christensen, N. D. and Kreider, J. W., *J. Virol.*, 64:3151–3165 (1990); Christensen, N. D., Kreider, J. W., Cladel, N. M., Patrick, S. D., and Welsh, P. A., *J. Virol.*, 64:5678–5681 (1990); and Jarrett, W. F. H., O'neil, B. W., Gaukroger, J. M., Smith, K. T., Laird, H. M., and Campo, M. S., *Vet. Rec.*, 126:437–475 (1990)) and, indeed, previous studies have demonstrated that the predominant antibody response detected against HPV-1 in humans is directed against such conformational epitopes (Steele, J. C., and Gallimore, P. H., *Virology*, 174:388–398 (1990); and Anisimová, E., Barták, P., Vlcek, D., Hirsch, I., Brichácek, B., and Vonka, V., *J. Gen. Virol.*, 71:419–422 (1990)). In the current study, we characterize a series of antibodies for their reactivity with HPV-1 conformational epitopes and demonstrate that HPV-1 L1 protein synthesized in cos cells expresses these virion conformational epitopes. This expressed protein can, therefore, be used for vaccine development as well as serologic screening techniques.

The initial experiments were designed to characterize a series of polyclonal and monoclonal antibodies for their reactivity with HPV-1 virions which were either in an intact (native conformation) or SDS-denatured (non-conformational) state. It was essential to characterize these antibodies in detail so that they could be used to evaluate the conformational state of expressed HPV-1 L1 protein. A summary of the ELISA experiments and the details for the isolation and purification of the HPV-1 virions are given in Table IV. Briefly, microtiter plate wells were coated with either intact or SDS-disrupted HPV-1 virions as described previously (Cowsert, L. M., Lake, P., and Jenson, A. B., *J. Natl. Cancer Inst.*, 79:1053–1057 (1987)) and used to screen the indicated antisera or monoclonal antibodies. The two hyperimmune rabbit sera produced against HPV-1 have been described previously (Pass, F., and Maizel, J. V., *J. Invest. Dermatol.*, 60:307–311 (1973)); rabbit (R #3) antiserum was generated against disrupted HPV-1 particles and rabbit (R #7) antiserum against intact particles. The four monoclonal antibodies that recognize conformational epitopes on the surface of HPV-1 particles were kindly provided by Dr. P. Pothier (Bourgogn University, France). Monoclonal antibody (MAB45) defines a linear epitope on the surface of the HPV-1 virion (Yaegashi, N., Jenison, S. A., Valentine, J. M., Dunn, M., Taichman, L. B., Baker, D. A., and Galloway, D. A., *J. Virol.*, 65:1578–1583 (1991)) and was obtained through the generosity of Dr. D. A. Baker (State University of New York, Stony Brook).

TABLE IV

Reactivity of rabbit polyclonal antisera and murine monoclonal antibodies with intact and disrupted HPV1 virions[a] as determined by ELISA.

| Antibody | | Immunogen | ELISA value | |
|---|---|---|---|---|
| | | | Intact virions | Disputed virions |
| Rabbit | Pass #7 | intact HPV1 | 1.493 | 0.002 |
| | Pass #3 | disrupted HPV1 | 0.918 | 0.616 |
| Murine | 334B6 | intact HPV1 | 0.438 | 0.003 |
| | 339B6 | intact HPV1 | 0.520 | 0.000 |
| | 405D5 | intact HPV1 | 0.429 | 0.009 |
| | D5 4G10 | intact HPV1 | 0.464 | 0.003 |
| | MAB45[b] | L1 of HPV1 | 0.512 | 0.332 |

[a]HPV-1 virions were extracted from productively infected plantar warts (Jenson, A. B., Lim, L. Y., and Singer, E., *J. Cutan. Pathol.*, 16:54–59 (1989)) and purified by equilibrium centrifugation in a CsCl gradient (Cowsert, L. M., Lake, P., and Jenson, A. B., *J. Natl. Cancer Inst.*, 79:1053–1057 (1987)). Virions (1.34 g/ml) and empty particles (1.29 g/ml) were collected separately, dialysed against Tris buffer (20 mM Tris, 10 mM PMSF, pH 7.5) and stored at −70° C. Microtiter plate wells (Immunolon II, Dynatech) were coated with either intact or SDS-disrupted HPV-1 virions as described previously (Cowsert, L. M., Lake, P., and Jenson, A. B., *J. Natl. Cancer Inst.*, 79:1053–1057 (1987)). The plates were then washed with PBS containing 0.05% Tween 20 (PBST). The microtiter wells were further incubated with PBS containing 1% bovine serum albumin (PBSA) for 1 hr at 37° C. to prevent nonspecific protein binding. The plates were washed again with PBST and incubated first with either rabbit polyclonal antibodies or murine monoclonal antibodies as primary antibody and subsequently with appropriate alkaline phosphatase-conjugated goat anti-IgG diluated 1:1000 in PBSA (Bio-Rad) for 1 hr at 37° C. Following several washes, the microtiter plates were developed with SIGMA 104 phosphatase substrate (Sigma) in diethanolamine buffer (Voller, A., Bidwell, D., and Bartlett, A., In "Manual of clinical immunology" (N. Rose and H. Freedman, Eds.), pp. 359–371. American Society of Microbiology, Washington, DC (1980)) for 30 min at 37° C. Absorbance was measured at 410 nm using a Dynatech Micro-elisa reader.
[b]MAB45 is an abbreviated designation for MABDW45 (Yaegashi, N., Jenison, S. A., Valentine, J. M., Dunn, M., Taichman, L. B., Baker, D. A., and Galloway, D. A., J. Virol., 65:1578–1583 (1991)).

The ELISA data indicate that R#7 antiserum indeed is specific for conformational epitopes on the surface of the HPV-1 virion since it reacts only with intact HPV-1 virions. This is also true for monoclonal antibodies 334B6, 339B6, 405D5, and D54G10. On the other hand, R#3 antiserum and monoclonal MAB45 also react well with SDS-denatured virions, demonstrating their reactivity with linear, non-conformational epitopes (Cowsert et al, *J. Natl. Cancer Inst.*, 79:1053–1057 (1987)).

To confirm the ELISA results shown in Table IV, we also evaluated the same antibodies for reactivity with disrupted HPV-1 virions as determined by Western blotting (FIG. 1). This figure demonstrates that only antibodies which recognized denatured HPV-1 virions by ELISA (R#3 and MAB45) showed significant reactivity with SDS-denatured virion proteins by immunoblotting. However, antibodies shown in Table IV to recognize only intact virions (R#7, 334B6, 339B6, D54G10, and 405D5) exhibited no or little reactivity by immunoblotting analysis. Thus, two independent techniques verify the specificity of the above antibodies for conformational and non-conformational epitopes on the HPV-1 virion.

In an attempt to produce isolated L1 protein which retained critical virion conformation epitopes, we expressed the HPV-1 L1 protein in mammalian cells. The HPV-L1 gene was amplified by PCR and cloned into the pSVL vector as described in FIG. 2 using standard molecular techniques (Maniatis, T., Fritsch, E. F., and Sambrook, J., In "Molecular Cloning: A Laboratory Manual," Cold Spring Harbor Laboratory, Cold Spring Harbor, N.Y. (1989)). The resulting plasmid, pSJ1-L1, expresses the HPV-1 L1 gene from a strong SV40 late promoter. In addition, the plasmid also contains the SV40 origin of replication and, when transfected into cos cells by calcium phosphate precipitation (Graham et al, *Virology*, 52:456–467 (1973)), replicates to a high copy number.

COS cells were first evaluated for L1 protein synthesis by immunoprecipitation techniques using the above antibodies. 48 hr post-transfection, the cos cells were labelled with $^{35}$S-methionine (NEN, Express $^{35}$S Protein labelling Mix) for 4 hr, washed with buffer, and solubilized in RIPA buffer (which contains a mixture of 1% NP-40, DOC, and 0.1% SDS detergents). The cell extracts were then immunoprecipitated with the indicated antibodies and analyzed by SDS-gel electrophoresis as previously described (Goldstei et al, *EMBO*, 9:137–146 (1990)). The data in FIG. 3 indicate that L1 protein could be efficiently precipitated by conformation-dependent antibodies (such as R#7, 334B6, 339B6, D54G10 and 405D5). In addition, the L1 protein could also be immunoprecipitated with antibodies which recognize non-conformational epitopes on the virion surface (R#3). These findings indicate that the L1 protein expressed in COS cells displayed conformational epitopes observed previously only on intact virions. It is also obvious that the L1 extraction conditions did not significantly denature the protein. Characteristic of L1 protein isolated directly from virions, the synthesized L1 protein was approximately 57 kD in size (Doorbar et al, *J. Virol.*, 61:2793–2799 (1987)). The retention of conformational epitopes in RIPA buffer and the ability of conformation-dependent antibodies to react with L1 indicates that the affinity purification of L1 protein from transfected cells will be possible.

COS cells were also evaluated for L1 protein synthesis by immunofluorescence microscopy (FIG. 4). Cells, plated onto glass coverslips in Dulbecco's modified Eagles medium (DMEM) supplemented with 10% fetal calf serum, were transfected with 10 μg plasmid DNA, glycerol-shocked 48 hr later, washed with phosphate buffered saline (PBS), and fixed for 5 min in cold acetone. The cells were then reacted with appropriate dilutions of primary antibody followed by fluorescein-conjugated goat anti-rabbit or goat anti-mouse IgG. Incubations with primary and secondary antibodies were performed at room temperature for 1 hr. Subsequent to a final PBS wash, the coverslips were mounted in Elvanol and viewed with an Olympus fluorescent microscope. The presence of L1 protein in cell nuclei was clearly discernible in 5–10% of transfected cells 48 hours post-transfection, independent of whether the primary antibody reacted with conformational and/or non-conformational epitopes. All of the antibodies which were capable of immunoprecipitating L1 were also successful by immunofluorescence. As mentioned previously, antibodies produced against disrupted virions recognize both internal and external virion linear epitopes and therefore are capable of reacting with intact particles (e.g., R#3). However, such antibodies do not recognize conformational epitopes and are not neutralizing (Ghim et al, Intl. J. Cancer, 49:285–289 (1991)). Thus, the staining pattern obtained with rabbit antisera to native (R#7) or denatured (R#3) HPV-1 virions was indistinguishable. These results, therefore, demonstrate unequivocally that the L1 protein synthesized in the cos cells was of a conformation similar to that found in intact virions. In addition, the protein clearly translocated to the nucleus in a normal fashion (Zhou et al, Virology, 185:625–632 (1991)).

The above findings suggest that the HPV-1 major capsid protein, when expressed in the absence of other viral proteins, can precisely reproduce/mimic the antigenicity of intact viral particles. While we cannot be certain that no assembled viral particles are present in the transfected cos cells, we have been unsuccessful in visualizing such structures by electron microscopic examination of either transfected cells or of immunoprecipitates containing L1 protein (data not shown). Apparently it is not essential to have viral particle formation in order to reproduce the characteristic, viral conformational epitopes.

Since the neutralization sites present on papillomavirus virions consist predominantly of conformational epitopes, it is inferred in our studies that the L1 protein synthesized in cos cells might serve successfully as a vaccine or for the serologic detection and typing of papillomavirus infections. Due to the similarities among the papillomaviruses with respect to genetic organization, virion structure, and amino acid sequence of their capsid proteins, it is also likely that our findings with HPV-1 L1 will have direct applicability to the study of other HPV's such as HPV-16 and HPV-18 which have important contributory roles to the development of cervical carcinoma.

TABLE V

ELISA VALUES AT 25 MIN IN SUBSTRATE
Four rabbits were inoculated with homogenates of COS cells containing intranuclear, conformationally correct BPV-1 L1. Each of 4 rabbits received homogenates of $1 \times 10^6$ cells in Freund's complete adjuvant on day 0, and $1 \times 10^6$ cells in Freund's incomplete adjuvant on days 14 and 28, and were then exsanguinated on day 38. Prebleed sera from the 4 rabbits were negative for reactivity with intact and denatured BPV-1 virions by ELISA. At day 38, rabbit #1 2, 3 and 4 were tested for reactivity with intact and disrupted BPV-1 particles after 25 min. incubation with substrate as shown in Table V.

|      | 1:50 | 1:100 | 1:500 |                        |
|------|------|-------|-------|------------------------|
| 1.   | .445 | .266  | .014  | Intact BPV-1 (I)       |
|      | .042 | .028  | .001  | Disrupted BPV-1(D)     |
|      | .016 | .001  | -.002 | Phosphate buffer saline (PBS) |
| 2.   | .332 | .210  | .011  | (I)                    |
|      | .076 | .047  | .077  | (D)                    |
|      | .025 | .018  | .001  | (PBS)                  |
| 3.   | .157 | .096  | .003  | (I)                    |
|      | .027 | .016  | -.001 | (D)                    |
|      | .022 | .011  | -.001 | (PBS)                  |
| 4.   | .275 | .159  | .011  | (I)                    |
|      | .075 | .044  | .005  | (D)                    |
|      | .017 | .011  | .001  | (PBS)                  |
| *1H8 | —    | —     | .022  | (I)                    |
|      | —    | —     | .880  | (D)                    |
|      | —    | —     | <.020 | (PBS)                  |

TABLE V-continued

ELISA VALUES AT 25 MIN IN SUBSTRATE
Four rabbits were inoculated with homogenates of COS cells containing intranuclear, conformationally correct BPV-1 L1. Each of 4 rabbits received homogenates of $1 \times 10^6$ cells in Freund's complete adjuvant on day 0, and $1 \times 10^6$ cells in Freund's incomplete adjuvant on days 14 and 28, and were then exsanguinated on day 38. Prebleed sera from the 4 rabbits were negative for reactivity with intact and denatured BPV-1 virions by ELISA. At day 38, rabbit #1 2, 3 and 4 were tested for reactivity with intact and disrupted BPV-1 particles after 25 min. incubation with substrate as shown in Table V.

|                  | 1:50 | 1:100 | 1:500  |       |
|------------------|------|-------|--------|-------|
| **Rabbit intact  | —    | —     | >2.000 | (I)   |
| BPV-1 Virions    | —    | —     | .058   | (D)   |
|                  | —    | —     | <.020  | (PBS) |

*MAb 1H8 recognizes only disrupted BPV-1
**Polyclonal Ab rabbit anti-intact BPV-1 recognized only intact BPV-1

EXAMPLE 4

This experiment describes the successful use of a formalin-inactivated canine oral wart homogenate as a vaccine to prevent infection by COPV in Beagle dogs. In this experiment, 26 dogs received doses of phosphate buffered saline (PBS) intradermally, and 99 dogs received two doses of a formalin-inactivated vaccine containing 50 ng of COPV L1 capsid protein. One month after the second dose, all 125 dogs were challenged with infectious COPV by scarification of the oral mucosa. All of the control group developed papillomavirus by 6–8 weeks after challenge. By contrast, none of the dogs immunized with the formalin-inactivated vaccine containing COPV L1 conformational capsid protein developed perceptible papillomas. The methodology of this experiment is described in detail below.

Materials and Methods

Equal numbers of male and female outbred Beagle dogs were obtained and maintained at Marshall Farms in North Rose, N.Y. The animals were vaccinated for parvovirus (31, 38, 45, and 59 days of age Northwest Tennessee Veterinary Services, Dresden, Tenn.); canine parainfluenza-*Bordatella bronchisepticum* (26 days of age, Intra-Trac-II, Schering-Plough Animal Health, Omaha, Nebr.); mink distemper (69 days of age, Distem-R TC, Schering-Plough Animal Health); canine distemper, adenovirus type-II, parainfluenza, parvovirus, and Leptospira (105 days of age, Duramune, $DA_2$ LP+PV, Fort Dodge Laboratories, Fort Dodge, Iowa); and rabies, (100 days of age, Imrab-1, Pitman-Moore, Mundelein, Ill.). Blood was drawn routinely at 120 days of age for CBC, reticulocyte count, and prothrombin times.

The dogs were nursed by their dams until 8 weeks and then put on a commercial diet. After weaning, the dogs were housed in open sheds in wire cages suspended above the ground. The dogs had access to tap water ad libitum. The dogs were on a natural light cycle.

Vaccine Preparation

Twenty-five (25) dogs were routinely inoculated as described below with live COPV in order to induce papillomas that produced infectious virions. After inoculation, the papillomas were removed surgically eight weeks after induction by scarification. The resultant papillomas were frozen in plastic vials and stored at −70° C. until used. For vaccine production or preparation of the challenge inoculum, papillomas were thawed, placed on two aluminum plates, and mascerated by hammering the plates together. The material was then placed in a blender with chlorinated tap water (2 grams of tissue into 100 ml total of water, 2% w/v) and homogenized for 10 minutes at room temperature. The homogenate was then passed twice through cheese cloth to remove large particulates and then frozen at −70° C. This preparation was thawed slowly to room temperature and then used to challenge dogs to induce productive oral papillomas or inactivated by the addition of 8 ml of neutral buffered 10% formalin to 240 mls (1:30 v/v) of the filtered homogenate, stored at 4° C. for 48 hours, and then used as the vaccine. This crude vaccine contained COPV L1 protein at concentrations ranging from 50–1000 ng/ml as determined by quantitative immunoblotting and ELISA techniques.

Animal Vaccination

All dogs were injected intradermally twice, at 8 and 10 weeks of age. For each injection, 0.2 ml of vaccine formulation was injected into the foot pad of the dew claw (phalanx) using a TB syringe with a 26 gauge needle. Twenty-six Beagle dogs received phosphate buffered saline, pH 7.4, as a placebo. Ninety-nine Beagle dogs received the formalin-inactivated vaccine in the same manner.

Challenge of Vaccinated Dogs and Control Groups

All 125 dogs were then challenged with infectious live COPV by scarification with a wire brush on the dorsal, buccal and maxillary mucosa. Challenge with infectious virus was performed one month after the second dose of vaccine or placebo solution. After challenge, each dog was examined daily by a clinical veterinarian or a trained veterinary technician for eight weeks.

Results

All of the control group dogs (26/26) which were injected with PBS and challenged with infectious COPV developed oral papillomas between six and eight weeks following exposure to the virus. By contrast, none of the dogs which were injected with the formalin-inactivated preparation (0/99) developed clinically evident oral papillomas. These results are believed to provide persuasive in vivo evidence that vaccination with wart extract containing conformationally correct L1 proteins may be used to protect Beagles against COPV infection. Additionally, given the substantial genetic and structural similarities between COPV and HPV, these results suggest that similar approaches may be applied for the prevention of HPV infections.

EXAMPLE 5

In this experiment, serum obtained from the above vaccinated weanling dogs was passively transferred to naive dogs. The recipient non-vaccinated dogs (which had received the immune serum transfer) were then evaluated for protection against COPV infection.

Materials and Methods

Serum samples were harvested by phlebotomy from either non-immune 10 week old naive beagle weanlings or from immune 12 week old weanlings which had been vaccinated with a crude COPV wart vaccine on weeks 8 and 10 following birth as described in Example 4. The serum immunoglobulin fraction was obtained from both groups by ammonium sulfate differential precipitation and dialysis against phosphate buffered saline.

After the immunoglobulin solutions were obtained from the non-immune and the immune dogs, these solutions were then administered intravenously to two groups of four dogs intravenously over a 20 minute period at a dosage of 200 mg/kg. Additionally, a control group of 4 dogs was administered lactate Ringers solution intravenously over a 20 minute period at a dosage of 200 mg.kg. These three groups of dogs were then challenged with infectious live COPV by scarification as described in Example 4.

Results

The results, of this experiments are illustrated in FIG. 5. As summarized therein, all the dogs which were administered lactate Ringers solution as well as the dogs which were administered non-immune dog serum developed papillomas after challenge with live infectious COPV. By contrast, none of the dogs who received the immune dog serum from the dogs which had been vaccinated with the crude COPV wart extract showed any signs of papillomas after challenge with live infectious COPV.

Therefore, these results provide evidence that immunity induced by the wart vaccine is mediated by immunoglobulins and that complete protection of animals can be achieved by these antibodies without the need or cooperation of cellular immune responses. This is a critical element in the design of a papillomavirus vaccine, whether it be for COPV or HPV.

Also important is the observation that the dose of challenge COPV used in this study was extremely high. Usually dogs require 6–8 weeks in order for tumors to become evident. However, in this specific experiment, a concentrated preparation of wart extract was used which generated tumors within 3 weeks. Thus, even when animals are challenged with extraordinarily high titers of virus, they are protected by passively transferred antibodies.

EXAMPLE 6

The previous two experiments described two critical elements in the development of a COPV vaccine containing: (1) the success of a formalin-inactivated wart extract containing COPV L1 proteins for conferring immunity against COPV in Beagle dogs and (2) the use of serum obtained from the above vaccinated dogs for the passive transfer of immunity. The final critical element, which is the object of this experiment, is to show that the isolated, conformationally-correct form of COPV L1 protein is the essential element in the vaccine which elicits immunity and that the COPV L1 protein is sufficient in itself in inducing protective immunity.

Materials and Methods

The following experiment relates to the use of conformationally correct recombinant COPV L1 proteins, in particular COPV L1 proteins expressed in recombinant baculovirus virus infected Sf9 cells, as a vaccine against COPV in Beagle dogs.

The COPV DNA was originally isolated and cloned by Dr. John Sundberg (Jackson Laboratories). Briefly, the COPV DNA was isolated from virions which had been purified by cesium chloride gradients from a canine oral papilloma. The COPV 8.2 kb DNA fragment has been cloned into a pBR322 at a unique Eco RI site. Sequencing of the genome (by the Sanger chain termination technique) was effected in collaboration with Dr. John Sundberg and Dr. Hijo Delius (Heidelberg, Germany). The L1 ORF extends from bp 5277 to bp 6785 (not including the termination codon which begins at 6786). For brevity, the amino acid translation of the DNA sequence is presented below and compared with the amino acid sequence of the HPV-1 L1 protein. Stars (*) indicate amino acid identities. The COPV L1 was compared with that of HPV-1 because the latter virus was the prototype HPV virus which we chose for expression using the pSVL vector (described in Example 3). However, given that the L1 protein is the most highly conserved protein of all the papillomavirus proteins, a comparison of the COPV L1 sequences with other papillomavirus L1 proteins would yield similar results.

This sequence analysis clearly indicates a high degree of homology between the HPV-1 and COPV L1 proteins, including the conservation of certain structural domains such as the positively charged carboxyl-terminus which has recently been shown to mediate nuclear translocation. The COPV L1 protein [SEQ ID NO.:2] is predicted to consist of 503 amino acids compared to the HPV-1 L1 protein [SEQ ID NO.:1] of 508 amino acids.

L1 Protein Sequences

Two weeks after completing the second administration of vaccine, all the animals were challenged with live, infectious COPV by scarification with a wire brush as in Example 4. Dogs were then evaluated weekly after challenge to detect oral papillomas for 10 weeks.

Results

In the control group of beagles (given phosphate buffered saline for vaccination), six of eight animals (Group I) developed oral tumors. By contrast, none (zero of thirty-two) of the dogs which were injected with formalin-fixed wart extract or any of the recombinant L1 protein-containing compositions showed any signs of oral tumors after challenge.

These results are summarized in FIG. 6 and establish that recombinant conformationally correct L1 proteins may be

```
HPV-1  MYNVFQMAVWLPAQNKFYLPPQPITRILSTDEYVTRTNLFYHATSRLLL
        *         ** ******* ******** *   ******* *** **** ****
COPV   M------AVWLPAQNKFYLPPQPSTKVLSTDEYVSRTNIFYHASSRLLT

HPV-1  VGHPLFEI---SSNQTVTIPKVSPNAFRVFRVRFADPNRFAFGDKAIFNP
        ****  **          *  ******  ****     *** ******  *  *
COPV   VGHPFYEIYKEERSEEVIVPKVSPNQYRVFRLLLPDPNNFAFGDKSLFDP

HPV-1  ETERLVWGLRGIEIGRGQPLGIGITGHPLLNKLDDAENPTNYINTHANG-
        *  *  * ******* ********** ****       *  ***       *   *
COPV   EKERLVWGLRGLEIGRGQPLGISVTGHPTFDRYNDVENPNKNLAGHGGGT

HPV-1  DSRQNTAFDAKQTQMFLVGCTPASGEHWT-SRRCPGEQVKLGDCPRVQMI
        ***  *     * ******    ** ** ****    *  *  *       *  **
COPV   DSRVNMGLDPKQTQMFMIGCKPALGEHWSLTRWCTGQVHTAGQCPPIELR

HPV-1  ESVIEDGDMMDIGFGAMDFAALQQDKSDVPLDVVQATCKYPDYIRMNHEA
           ****** ********** ***   ** ** *  *    ******  *   *
COPV   NTTIEDGDMVDIGFGAMDFKALQHYKSGVPIDIVNSACKYPDYLKMANEP

HPV-1  YGNSMFFFARRRQMYTRHFFTRGGSVGDKEAVPQSLYLTADAEPRTTLAT
        **     ***  ****  *  **     *  *   *   *  **     *  *          *
COPV   YGDRCFFFVRRRQLYARHIMSRSGTQG-LEPVPKDTYATREDN---NIGT

HPV-1  TNYVGTPSGSMVSSDVQLFNRSYWLQRGQGQNNGIGWRNQLFITVGDNTR
        ***    ***** ***   ***** **  **  **  **** *  **** *    ****
COPV   TNYFSTPSGSLVSSEGQLFNRPYWIQRSQGKNNGIAWGNQLFLTVVDNTR

HPV-1  GTSLSIS---MKNNASTTYSNANFNDFLRHTEEFDLSFIVQLCKVKLTPE
        ** * *            *             *** **     * ********** **
COPV   GTPLTINIGQQDKPEEGNYVPSSYRTYLRHVEEYEVSIIVQLCKVKLSPE

HPV-1  NLAYIHTMDPNILEDWQLSVSQPPTNPLEDQYRFLGSSLAAKCPEQAPPE
        *** ********* *** *     **    *  *  **      *** ***     **
COPV   NLAIIHTMDPNIIEDWHLNVT-PPSGTLDDTYRYI-NSLATKCPTNIPPK

HPV-1  PQTDPYSQYKFWEVDLTERMSEQLDQFPLGRKFLYQSGMTQRTATSSTTK
            **       *******     *  ***** *******  *         *
COPV   TNVDPFRDFKFWEVDLKDKMTEQLDQTPLGRKFLFQTN-VLRPRSVKVRS

HPV-1  RTTVRVSTSAKRRKA
            *  *     *  *
COPV   TSHVSVKRKAVRKRK
```

In this experiment, 40 dogs were vaccinated at 8 and 10 weeks of age with 0.2 ml of several vaccine formulations. The injections were performed in the foot pad as described previously in Example 4. The recombinantly-expressed L1 protein was examined in the electron microscope and found to assemble into virus-like particles and, more importantly, to react with antiserum that was specific for COPV conformational capsid surface epitopes. The first control group of dogs was mock-vaccinated with phosphate buffered saline (Group I), and the second group of dogs was vaccinated with formalin-fixed wart homogenates (Group II) as described in Example 4. The third group was vaccinated with 20 μg protein contained in phosphate buffered saline (Group III), the fourth group with 20 μg of L1 protein in PBS containing alum (Group IV), and the fifth group with 20 μg L1 protein in QS21 adjuvant (Group V).

used as an effective vaccine against COPV in Beagle dogs. This experiment also indicates that COPV L1 protein is sufficient (in the absence of viral L2 capsid protein as well as other cellular proteins in the wart extract) to completely protect against infectious COPV challenge. Moreover, given the substantial similarities between COPV and human papillomavirus, these results provide further evidence that conformationally correct human papillomavirus L1 proteins may be used as an effective vaccine against human papillomavirus infection.

To further establish the importance of L1 conformation, the antibody response against both linear and conformational COPV L1 epitopes was compared after the first vaccination, after the second vaccination, and after challenge with infectious COPV. These results are summarized in FIG. 7 and FIG. 8. It can be seen from these figures that the Beagle dogs which were inoculated with the wart extract or with the recombinant conformationally correct COPV L1 proteins exhibit a substantial antibody response against COPV conformational epitopes. By contrast, the control group exhibited virtually no change in the antibody response to conformational epitopes after challenge.

While vaccinated animals clearly developed an immune response to conformational L1 epitopes, they failed to develop a significant response to linear (non-conformational epitopes) as demonstrated in FIG. 7. This provides further evidence that antibodies to linear epitopes are not involved in protection.

Group 4 animals, which were inoculated with the recombinant L1 protein in alum, had the highest linear epitope antibody response. This suggests that the alum adjuvant may partially affect the L1 protein's conformational structure, thereby exposing linear L1 epitopes to the dog's immune system.

EXAMPLE 7

Example 3 of this application demonstrates that the HPV-1 L1 protein (when expressed by an SV40 vector in COS cells) reproduces conformational epitopes of intact HPV-1 virions. In addition, the L1 capsid protein was translocated into the cell nucleus, was of appropriate size (57 kb), and could be isolated as a conformational protein by immunoprecipitation techniques. As discussed supra, based on these results and because of the similarities between different papillomaviruses with respect to genetic organization, virion structure, and amino acid sequence of capsid proteins, these results have direct applicability to other PV L1 proteins, including HPVs such as HPV-6, HPV-11, HPV-16, and HPV-18 as well as L1 sequences of other species origin including, e.g., COPV and equine papillomavirus.

Therefore, using the exact same methodology as above, the COPV L1 sequence and fragments thereof were expressed by an SV40 vector in COS cells. It was found that the COPV L1 sequence was expressed in proper conformation as demonstrating by reactivity with conformationally-dependent antibodies.

By contrast, it was found that expression of COPV L1 sequences containing deletions in the amino-terminus portion of the DNA resulted in L1 proteins which did not exhibit the correct conformation. These results suggest that the amino-terminus portion of the L1 sequence may be involved in the folding of the L1 protein and its proper conformation.

However, expression of a COPV L1 DNA lacking the codons encoding the 26 amino acids at the carboxy-terminus of the L1 protein and which were replaced by a 5 amino acid nuclear signal sequence of a nonstructural viral protein of SV40, in COS cells was found to result in COPV L1 proteins which were translocated into cell nuclei and exhibited conformational epitopes. Therefore, these results provide convincing evidence that PV L1 DNA fragments may also be used to produce conformational L1 proteins. More specifically, these results substantiate that PV L1 DNA sequences which lack a portion of the carboxy-terminal portion of the L1 sequence result in conformational L1 proteins. Moreover, other L1 fragments which upon expression give rise to conformational L1 proteins may be identified by immunodetection, e.g., by screening for reactivity with antibodies specific to conformational L1 epitopes.

EXAMPLE 8

To further confirm that it is not necessary for the L1 protein to assemble into virus-like particles to elicit a protective response against PV infection and the subsequent formation of papillomas, an additional experiment was conducted using L1 protein expressed using the above-described SV40 vector/COS cell expression system. This system was selected because the results of previous multiple electron microscopy studies have indicated that PV pseudocapsids are not produced by COS cells.

The entire COPV L1 sequence was expressed using an SV40 vector in COS cells. Using substantially the same protocol as described supra, naive beagle dogs were inoculated intradermally with a formalin-fixed crude extract of COS cells expressing the entire COPV L1 protein.

The results of this experiment demonstrated that of five beagles inoculated with the formalin-fixed crude extract of COS cells expressing COPV L1 protein, four were completely protected upon intraoral challenge with infectious COPV. Therefore, this provides convincing in vivo evidence that COPV L1 proteins expressed in COS cells can be used as an effective vaccine for providing immunity against COPV infection.

These results also indicate that PV conformationally correct L1 proteins alone or linked together as capsomeres, but not self-assembled as a pseudovirus particle are capable of eliciting neutralizing antibodies that protect against the formation of papillomas. Also, these results provide further evidence that it is not necessary for the L1 protein to assemble into virus-like particles to elicit a protective response against PV infection and the subsequent formation of papillomas.

EXAMPLE 9

To demonstrate the exquisite specificity of canine antibodies produced against conformational epitopes of COPV L1 protein, a second large vaccine study was conducted in weanling beagles. Forty-two beagles were inoculated intradermally at 8 and 10 weeks of age with the following vaccine preparations: 14 received COPV L1 VLPs alone; 7 received formalin-inactivated oral COPV L1 proteins; 7 received an extract of the vector alone, and 7 received saline solution. All beagles were challenged orally with infectious COPV at 12 weeks of age and followed for development of oral cavity papillomas. None of 21 beagles receiving either COPV L1 VLPs or formalin-inactivated papillomas developed oral cavity papillomas. Twenty-seven of 28 of the remaining beagles developed florid oral papillomatosis. All of the beagles receiving either denatured COPV L1 proteins (nonconformational L1 proteins; 7 of 7) or HPV-11 L1 VLPs (7 of 7) developed extensive, large oral papillomas. This is highly significant scientific evidence that conformationally correct COPV-L1 protects against COPV-induced oral papillomas, and that this protection is COPV L1 type specific since there was no protection conferred by vaccination with the HPV-11 VLP (HPV-11 is the prototype oral human papillomavirus that infects and causes papillomas in the oral cavity).

Now having fully described this invention, it will be understood by those with skill in the art that this invention may be performed within a wide and equivalent range of conditions, parameters, and the like, without affecting the spirit or scope of the invention or any embodiment thereof.

All references cited herein are incorporated by reference in their entirety as if individually incorporated by reference.

What is claimed is:

1. A method of protecting canines against canine oral papillomavirus (COPV) infection comprising administering a prophylactically effective amount of formalin-inactivated COPV.

2. A method of protecting canines against canine oral papillomavirus (COPV) infection comprising administering a prophylactically effective amount of recombinant COPV L1 protein or a COPV L1 protein that comprises a deletion in the carboxy-terminal portion of said L1 protein which L1 or a fragment comprising a carboxy-terminal deletion exhibits the conformation of COPV L1 proteins expressed on intact COPV virions.

3. The method of claim 2 wherein said COPV L1 protein or fragment is expressed in insect cells using a baculovirus expression system.

4. The method of claim 3 wherein said COPV L1 protein is expressed in COS cells.

5. The method of claim 2 wherein said L1 protein lacks at least 26 of the carboxy-terminal amino acid residues.

6. A vaccine for conferring protection against COPV infection in canines which comprises: (i) the prophylactically effective amount of COPV L1 protein or a COPV L1 protein containing a deletion in the carboxy-terminal portion of said protein which exhibits the conformation of COPV L1 proteins expressed on intact COPV L1 virions; and (ii) a pharmaceutically-acceptable carrier.

7. The vaccine of claim 6 wherein the vaccine further comprises an adjuvant.

8. The vaccine of claim 7 wherein said adjuvant is selected from the group consisting of alum, saponin, and QS21.

9. The vaccine of claim 6 wherein said L1 fragment lacks at least 26 amino acids of the carboxy-terminal amino acids.

10. The vaccine of claim 9 wherein the deleted amino acids are replaced by a nuclear signal sequence.

11. The vaccine of claim 10 wherein said nuclear signal sequence is derived from a virus.

* * * * *

UNITED STATES PATENT AND TRADEMARK OFFICE
CERTIFICATE OF CORRECTION

PATENT NO. : 5,874,089
DATED : February 23, 1999
INVENTOR(S) : C. Richard Schlegel et al.

It is certified that error appears in the above-identified patent and that said Letters Patent is hereby corrected as shown below:

Title Page,

Please insert the following in Column 1:

Related U.S. Application Data

[60] Provisional Application Serial No. 60/004,691, Oct. 2, 1995, abandoned.

Signed and Sealed this

Thirty-first Day of July, 2001

Attest:

NICHOLAS P. GODICI
Attesting Officer     Acting Director of the United States Patent and Trademark Office